United States Patent
Nottle

(10) Patent No.: US 11,505,781 B2
(45) Date of Patent: Nov. 22, 2022

(54) COMPOSITIONS AND METHODS FOR MATURATION OF OOCYTES IN VITRO

(71) Applicant: The University of Adelaide, Adelaide (AU)

(72) Inventor: Mark Brenton Nottle, Bibaringa (AU)

(*) Notice: Subject to any disclaimer, the term of this patent is extended or adjusted under 35 U.S.C. 154(b) by 652 days.

(21) Appl. No.: 16/467,911

(22) PCT Filed: Dec. 8, 2017

(86) PCT No.: PCT/AU2017/051354
§ 371 (c)(1),
(2) Date: Jun. 7, 2019

(87) PCT Pub. No.: WO2018/102881
PCT Pub. Date: Jun. 14, 2018

(65) Prior Publication Data
US 2019/0382722 A1  Dec. 19, 2019

(30) Foreign Application Priority Data
Dec. 9, 2016  (AU) ................ 2016905096

(51) Int. Cl.
*C12N 5/075*  (2010.01)
(52) U.S. Cl.
CPC ........ *C12N 5/0609* (2013.01); *C12N 2501/22* (2013.01)
(58) Field of Classification Search
CPC . C12N 5/0609; C12N 2501/22; C07K 14/535
USPC ....................................................... 435/377
See application file for complete search history.

(56) References Cited

U.S. PATENT DOCUMENTS

2002/0028509 A1  3/2002  Choay et al.
2012/0252119 A1  10/2012  Gilchrist et al.

OTHER PUBLICATIONS

Gimeno (2011, Veterinary Research, 42: 9, pp. 1-10).*
Robertson, "GM-CSF regulation of embryo development and pregnancy," *Cytokine & Growth Factor Reviews*, vol. 18, pp. 287-298, 2007.
Maliszewski et al., "Bovine GM-CSF: molecular cloning and biological activity of the recombinant protein," *Molecular Immunology*, vol. 25, No. 9, pp. 843-850, 1988.
Cheong et al., "Improvement in the blastocyst quality and efficiency of putative embryonic stem cell line derivation from porcine embryos produced in vitro using a novel culturing system," *Molecular Medicine Reports*, vol. 12, pp. 2140-2148, 2015.
Cui et al., "Mouse granulocyte-macrophage colony-stimulating factor enhances viability of porcine embryos in defined culture conditions," *Animal Reproductive Science*, vol. 84, pp. 169-177, 2004.
Economou et al., "The combination of calcium ionophore A23187 and GM-CSF can safely salvage aged human unfertilized oocytes after ICSI," *Journal of Assisted Reproduction and Genetics*, vol. 34, No. 1, pp. 33-41, 2016.
International Preliminary Report on Patentability in PCT/AU2017/051354, dated Apr. 4, 2019 (25 pages).
Gilchrist et al., "Effect of granulocyte-macrophage colony-stimulating factor deficiency on ovarian follicular cell function," *Journal of Reproduction and Fertility*, vol. 120, pp. 283-292, 2000.
Peralta et al., "Granulocyte-macrophage colony stimulating factor (GM-CSF) enhances cumulus cell expansion in bovine oocytes," *Reproductive Biology and Endocrinology*, vol. 11, No. 1, article 55, 2013 (12 pages).
Sondij et al., "Effect of GM-CSF and IL-6 on Meiotic Resumption of Bovine Oocytes In Vitro and their Subsequent Fertilization and Developmental Competence," Abstract P46, *Reproduction in Domestic Animals*, vol. 39, No. 4, p. 274, 2004 (1 page).

* cited by examiner

*Primary Examiner* — Valarie E Bertoglio
(74) *Attorney, Agent, or Firm* — Klarquist Sparkman, LLP

(57) ABSTRACT

The present invention relates to culture media for oocytes and uses thereof. Specifically, media for culturing an oocyte in vitro are disclosed, wherein said media comprise granulocyte macrophage-colony stimulating factor (GM-CSF). The presence of GM-CSF in the media increases the maturation and/or developmental competence of the oocyte making it suitable for use in subsequent assisted reproductive technologies. Methods for increasing the maturation and/or developmental competence of an oocyte are also disclosed.

6 Claims, 5 Drawing Sheets
Specification includes a Sequence Listing.

COMPOSITIONS AND METHODS FOR MATURATION OF OOCYTES IN VITRO

PRIORITY CLAIM

This application claims priority from Australian provisional patent application number 2016905096 filed on 9 Dec. 2016, the contents of which are to be taken as incorporated herein by this reference.

FIELD OF THE INVENTION

The present invention relates generally to compositions and methods for the maturation of oocytes. In particular, the present invention relates to compositions and in vitro methods that utilise an improved maturation medium, which increases maturation of oocytes prior to fertilisation.

BACKGROUND OF THE INVENTION

In mammals, immature eggs (oocytes) grow and develop in follicles within the ovary. Immature oocytes are metabolically coupled to somatic granulosa cells, which surround the oocyte and nurture the development of the oocyte until ovulation. Essentially, maturation of the oocyte depends on its association with its companion somatic granulosa cells (termed cumulus cells once the oocyte is ovulated) which not only support its growth and development, but also regulate the progression of meiosis.

The cytoplasmic and nuclear maturation of the oocyte during pre-ovulatory development are closely related but differentially distinguishable processes crucial for successful fertilisation, development of the embryo, and also for the ability of the embryo to implant, develop to term and produce healthy offspring.

During cytoplasmic development, the diameter of the oocyte substantially increases from ~15 to 100 μm, corresponding to a 300-fold increase in volume. At this stage the oocyte is both transcriptionally and translationally very active. For example, a mature mouse oocyte contains ~200-fold more RNA and ~50-60-fold more protein than an average somatic cell. The content of mRNA in the oocyte is also high, ~15-20%, compared to that of ~2-3% in a somatic cell.

Nuclear maturation of the oocyte occurs after the gonadotropin luteinising hormone surge, and involves the dissolution of the nuclear membrane, chromosome condensation followed by orientation in the equatorial plate, and organisation of the microtubules in a spindle.

A significant proportion of children in western countries are now born using assisted reproduction technologies, including the use of in vitro fertilization (IVF). IVF generally takes the form of hormonally stimulating the ovaries of women to produce multiple growing follicles, collecting the ova from these preovulatory follicles, fertilizing collected ova with sperm in vitro and introducing the resultant embryo into the uterus. Given that a number of these steps occur outside of the reproductive tract, mimicking the natural environment of the oocyte is an important consideration towards maximizing the success of an IVF program.

Large doses of gonadotropin, or other ovarian follicle stimulating agents used in standard IVF procedures, can lead to a condition of ovarian hyperstimulation syndrome (OHSS), which occurs in approximately 5% of women undertaking IVF cycles. OHSS is usually mild and self-limiting. In some cases, urgent medical attention is required. When severe, the condition can be potentially life threatening requiring hospitalization, intravenous fluids, pain relief, and other medication. Pulmonary embolism from a clot in the leg or complications of severe dehydration may occur in rare cases.

In vitro maturation (IVM) of oocytes prior to fertilization is increasingly used an adjunct therapy to IVF, which greatly reduces the requirement for hormone administration during treatment. IVM involves the removal of ova from smaller follicles in patients who receive either low levels of gonadotropin or even no gonadotropin. The procedure used to obtain eggs requires a modified patient management system and ova pick-up procedure.

Women with the condition of polycystic ovarian syndrome require IVM in preference to IVF to avoid ovarian hyperstimulation caused by the administration of gonadotropin, or other ovarian follicle stimulating agents. IVM is also applied to women who have been advised to minimize follicle stimulation during infertility treatment, and is used in female cancer patients undergoing chemotherapy and who are requiring fertility preservation. IVM is also more convenient to the patient as it requires less drug administration, which is usually performed by the patients themselves. Therefore, IVM has cost advantages, as the cost of drug use is minimized.

Nevertheless, the efficiency of IVM relative to IVF in establishing pregnancies and live births are reduced. Although there have been some improvements in recent times to patient management, there has been little advance in laboratory techniques despite the fact that current IVM methods do not replicate the environment in the maturing follicle and reproductive tract.

In non-human mammals, in vitro production (IVP) of animal embryos has a variety of purposes, such as genetic improvement in livestock and domesticated breeds, genetic rescue in rarer breeds, as well as a platform technology for manipulations, such as production of sexed embryos from sexed sperm, or cloning by somatic cell nuclear transfer. An essential technique in the production of embryos in vitro is the maturation of oocytes in vitro. IVP has the potential to replace current conventional techniques such as multiple ovulation and embryo transfer (MOET), where (similarly to human clinical application) gonadotropin treatment is required. However, adoption of IVP for breeding and other uses has been hampered by the relatively low efficiencies of producing transferable stage embryos, the poor results following embryo transfer of such embryos and the poor results following freezing and thawing (storage) of such embryos. The immaturity of oocytes used for IVP of animal embryos is reflective of these poor results.

Accordingly, new compositions and methods for maturing oocytes in vitro, for example to improve the effectiveness of assisted reproductive technologies, are highly desirable.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is predicated, in part, on the finding that granulocyte macrophage-colony stimulating factor (GM-CSF) is effective at increasing the maturation and developmental competence of an oocyte in vitro. This enables the formulation and preparation of media for use in in vitro maturation of oocytes, including as part of reproductive technology applications.

Accordingly, in a first aspect, the present invention provides an in vitro oocyte maturation medium, the medium comprising granulocyte macrophage-colony stimulating factor (GM-CSF).

In a second aspect, the present invention provides a medium for increasing maturation of an oocyte in vitro, the medium comprising granulocyte macrophage-colony stimulating factor (GM-CSF).

In a third aspect, the present invention provides an in vitro culture medium when used for increasing maturation of an oocyte, the medium comprising granulocyte macrophage-colony stimulating factor (GM-CSF).

In some embodiments of the first to third aspects of the invention, the GM-CSF increases the developmental competence of an oocyte cultured in the medium. Development competence may be measured, for example, in vitro by an increase in cleavage rate, on time blastocyst development and/or development to the blastocysts stage.

In some embodiments of the aforementioned aspects of the invention, an embryo derived from an oocyte cultured in the medium has one or more of an increased blastocyst inner cell mass number, increased blastocyst rate, increased trophectoderm cell number, increased blastocyst total cell number, and increased viability.

In some embodiments of the aforementioned aspects of the invention, a blastocyst derived from an oocyte cultured in the medium has decreased DNA damage. A decrease in DNA damage may in turn reduce or normalize abherrant gene expression, which may be a consequence of in vitro culture.

In some embodiments of the aforementioned aspects of the invention, one or more of implantation, pregnancy rate, and development to term in a surrogate following transfer of an embryo derived from an oocyte cultured in the medium to the surrogate is increased.

In some embodiments of the aforementioned aspects of the invention, the oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

In some embodiments of the aforementioned aspects of the invention, the oocyte is from an aged and/or obese subject.

In some embodiments of the aforementioned aspects of the invention, the GM-CSF is species-specific. In some embodiments, the amount of GM-CSF present in the medium is about 0.1 ng/ml to about 100 ng/ml.

In a fourth aspect, the present invention provides a method of in vitro maturation of an oocyte, the method comprising culturing the oocyte in a medium of any one of the first to third aspects of the invention.

In a fifth aspect, the present invention provides an oocyte matured by the method of the fourth aspect of the invention.

In a sixth aspect, the present invention provides an embryo or non-human animal produced from the oocyte of the fifth aspect of the invention.

In a seventh aspect, the present invention provides a method of increasing maturation of an oocyte in vitro, the method comprising culturing the oocyte in a medium comprising granulocyte macrophage-colony stimulating factor (GM-CSF).

In an eighth aspect, the present invention provides a method of increasing developmental competence of an oocyte in vitro, the method comprising culturing the oocyte in a medium comprising granulocyte macrophage-colony stimulating factor (GM-CSF).

In some embodiments of the seventh and eighth aspects of the invention, an embryo derived from the oocyte has one or more of an increased blastocyst inner cell mass number, increased blastocyst rate, increased trophectoderm cell number, increased blastocyst total cell number, and increased viability.

In some embodiments of the seventh and eighth aspects of the invention, a blastocyst derived from an oocyte cultured in the medium has decreased DNA damage.

In some embodiments of the seventh and eighth aspects of the invention, one or more of implantation, pregnancy rate, and development to term, in a surrogate following transfer of an embryo derived from an oocyte cultured in the medium to the surrogate is increased.

In some embodiments, the method is used as part of an assisted reproductive technology.

In some embodiments of the seventh and eighth aspects of the invention, the oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

In some embodiments of the seventh and eighth aspects of the invention, the oocyte is from an aged and/or obese subject.

In some embodiments of the seventh and eighth aspects of the invention, the GM-CSF is species-specific. In some embodiments, the amount of GM-CSF present in the medium is about 0.1 ng/ml to about 100 ng/ml.

In a ninth aspect, the present invention provides a method of producing an embryo from an oocyte by an assisted reproductive technology, the method comprising:
  (a) collecting an oocyte from an ovary of a subject;
  (b) culturing the oocyte in vitro in a medium comprising GM-CSF; and
  (c) producing an embryo from the oocyte by fertilising the oocyte in vitro.

In some embodiments, one or more of implantation, pregnancy rate, and development to term, in a surrogate following transfer of the embryo to the surrogate is increased.

In some embodiments of the ninth aspect of the invention, the oocyte is collected from an aged and/or obese subject.

In some embodiments, sperm used in the assisted reproductive technology is cultured in a medium comprising GM-CSF prior to fertilisation of the oocyte.

In some embodiments, fertilisation of the oocyte takes place in a medium comprising GM-CSF.

In some embodiments of the ninth aspect of the invention, the method further comprises the step of culturing the embryo once produced in a medium comprising GM-CSF.

In a tenth aspect, the present invention provides a method of assisted reproduction involving an oocyte, the method comprising the step of culturing the oocyte in vitro in a medium comprising GM-CSF.

In an eleventh aspect, the present invention provides a method of assisted reproduction involving an oocyte, the method comprising the step of in vitro maturation of an oocyte by culturing the oocyte in vitro in a medium comprising GM-CSF.

In some embodiments of the tenth and eleventh aspects of the invention, the method comprises the further step of fertilizing the oocyte in vitro with sperm that has been cultured in a medium comprising GM-CSF.

In some embodiments of the tenth and eleventh aspects of the invention, the method comprises the further step of culturing an embryo derived from the oocyte in vitro in a medium comprising GM-CSF. In some embodiments, one or more of implantation, pregnancy rate, and development to term, in a surrogate following transfer of the embryo to the surrogate is increased.

In some embodiments of the tenth and eleventh aspects of the invention, the oocyte is collected from an aged and/or obese subject.

In a twelfth aspect, the present invention provides granulocyte macrophage-colony stimulating factor (GM-CSF) for use, or when used, in a culture medium for increasing maturation of an oocyte in vitro or for increasing developmental competence of an oocyte in vitro.

In some embodiments of the twelfth aspect of the invention, an embryo derived from the oocyte cultured in the culture medium has one or more of an increased blastocyst inner cell mass number, increased blastocyst rate, increased trophectoderm cell number, increased blastocyst total cell number, and increased viability.

In some embodiments of the twelfth aspect of the invention, a blastocyst derived from an oocyte cultured in the medium has decreased DNA damage.

In some embodiments, the GM-CSF is used in a culture medium as part of an assisted reproductive technology. In one embodiment, the assisted reproductive technology is in vitro fertilization.

In some embodiments of the twelfth aspect of the invention, one or more of implantation, pregnancy rate, and development to term in a surrogate following transfer of an embryo derived from an oocyte cultured in the medium to the surrogate is increased.

In some embodiments of the twelfth and thirteenth aspects of the invention, the oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

In some embodiments of the twelfth aspect of the invention, the oocyte is from an aged and/or obese subject.

In some embodiments of the twelfth and thirteenth aspects of the invention, the GM-CSF is species-specific. In some embodiment, the amount of GM-CSF present in the medium is about 0.1 ng/ml to about 100 ng/ml.

In a thirteenth aspect, the present invention provides use of granulocyte macrophage-colony stimulating factor (GM-CSF) in the preparation of a culture medium for increasing maturation of an oocyte in vitro or for increasing developmental competence of an oocyte in vitro.

In some embodiments, an embryo derived from the oocyte cultured in the culture medium has one or more of an increased blastocyst inner cell mass number, increased blastocyst rate, increased trophectoderm cell number, increased blastocyst total cell number, and increased viability.

In some embodiments of the thirteenth aspect of the invention, a blastocyst derived from an oocyte cultured in the medium has decreased DNA damage.

In some embodiments, the culture medium is used as part of an assisted reproductive technology. In one embodiment, the assisted reproductive technology is in vitro fertilization.

In some embodiments of the thirteenth aspect of the invention, one or more of implantation, pregnancy rate, and development to term in a surrogate following transfer of an embryo derived from an oocyte cultured in the medium to the surrogate is increased.

In some embodiments of the thirteenth aspect of the invention, the oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

In some embodiments of the thirteenth aspect of the invention, the oocyte is from an aged and/or obese subject.

In some embodiments of the thirteenth aspect of the invention, the GM-CSF is species-specific. In some embodiments, the amount of GM-CSF present in the medium is about 0.1 ng/ml to about 100 ng/ml.

In a fourteenth aspect, the present invention provides a combination product for use in, or when used for, increasing maturation of an oocyte in vitro or for increasing developmental competence of an oocyte in vitro, the combination product comprising:
(i) a culture medium;
(ii) granulocyte macrophage-colony stimulating factor (GM-CSF); and optionally
(iii) instructions for culturing an oocyte in the culture medium comprising the GM-CSF.

In a fifteenth aspect, the present invention provides a combination product for use in, or when used for, increasing maturation of an oocyte in vitro or for increasing developmental competence of an oocyte in vitro, the combination product comprising:
a culture medium comprising granulocyte macrophage-colony stimulating factor (GM-CSF); and
(ii) instructions for culturing an oocyte in the culture medium.

In some embodiments of the fourteenth and fifteenth aspects of the invention, an embryo derived from the oocyte cultured in the culture medium comprising the GM-CSF has one or more of an increased blastocyst inner cell mass number, increased blastocyst rate, increased trophectoderm cell number, increased blastocyst total cell number, and increased viability.

In some embodiments of the fourteenth and fifteenth aspects of the invention, a blastocyst derived from an oocyte cultured in the medium has decreased DNA damage.

In some embodiments, the combination product is used as part of an assisted reproductive technology. In one embodiment, the assisted reproductive technology is in vitro fertilization.

In some embodiments of the fourteenth and fifteenth aspects of the invention, one or more of implantation, pregnancy rate, and development to term in a surrogate following transfer of an embryo derived from an oocyte cultured in the medium to the surrogate is increased.

In some embodiments of the fourteenth and fifteenth aspects of the invention, the oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

In some embodiments of the fourteenth and fifteenth aspects of the invention, the oocyte is from an aged and/or obese subject.

In some embodiments of the fourteenth and fifteenth aspects of the invention, the GM-CSF is species-specific.

BRIEF DESCRIPTION OF THE FIGURES

For a further understanding of the aspects and advantages of the present invention, reference should be made to the following detailed description, taken in conjunction with the accompanying figures.

DETAILED DESCRIPTION OF THE INVENTION

Figure 1:
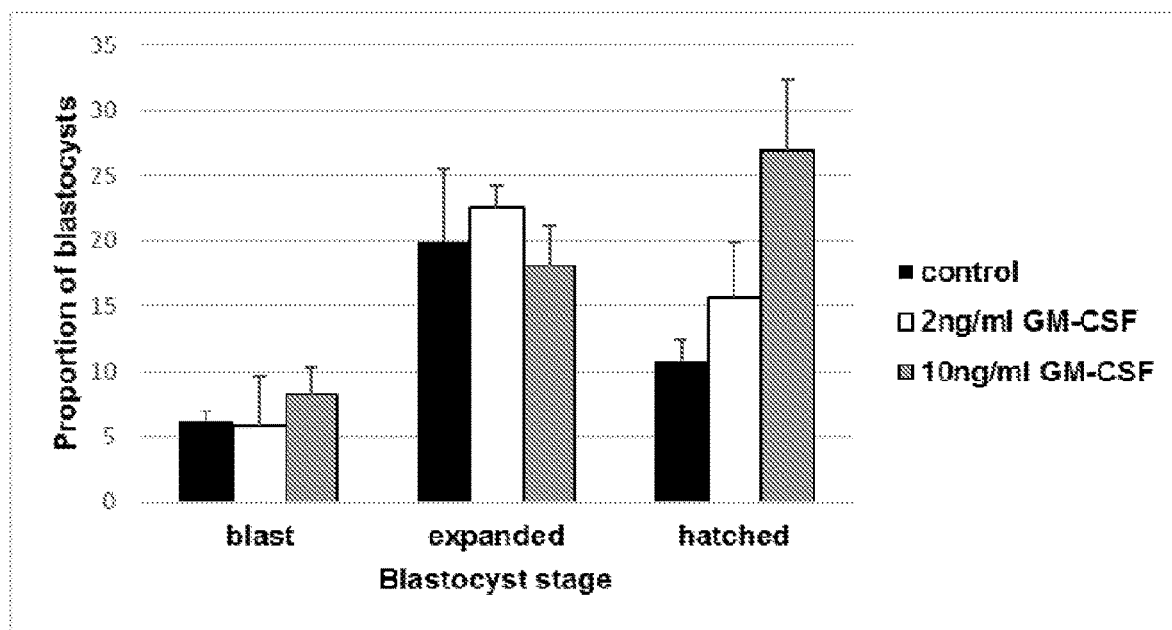
FIG. 1—a graph showing the effect of adding GM-CSF to oocyte maturation media on the proportion of blastocysts that had hatched by day 8 of culture. The addition of 2 ng/ml and 10 ng/ml of bovine GM-CSF to oocyte maturation media increased the proportion of hatched bovine blastocysts on day 8 of embryo culture by 45.4% and 149.0% respectively, compared with a control. 0 ng (control; black), 2 ng/ml GM-CSF (white), and 10 ng/ml GM-CSF (grey). Values mean±SEM of five replicates.

Nucleotide and polypeptide sequences are referred to herein by a sequence identifier number (SEQ ID NO:). A summary of the sequence identifiers is provided in Table 1. A sequence listing has also been provided at the time of filing this application.

TABLE 1

Summary of sequence identifiers

| Sequence Identifier | Sequence |
| --- | --- |
| SEQ ID NO: 1 | Human GM-CSF nucleotide sequence |
| SEQ ID NO: 2 | Human GM-CSF amino acid sequence |
| SEQ ID NO: 3 | Bovine GM-CSF nucleotide sequence |
| SEQ ID NO: 4 | Bovine GM-CSF amino acid sequence |
| SEQ ID NO: 5 | Porcine GM-CSF nucleotide sequence |
| SEQ ID NO: 6 | Porcine GM-CSF amino acid sequence |
| SEQ ID NO: 7 | Equine GM-CSF nucleotide sequence |
| SEQ ID NO: 8 | Equine GM-CSF amino acid sequence |
| SEQ ID NO: 9 | Canine GM-CSF nucleotide sequence |
| SEQ ID NO: 10 | Canine GM-CSF amino acid sequence |
| SEQ ID NO: 11 | Feline GM-CSF nucleotide sequence |
| SEQ ID NO: 12 | Feline GM-CSF amino acid sequence |
| SEQ ID NO: 13 | Murine GM-CSF nucleotide sequence |
| SEQ ID NO: 14 | Murine GM-CSF amino acid sequence |
| SEQ ID NO: 15 | Ovine GM-CSF nucleotide sequence |
| SEQ ID NO: 16 | Ovine GM-CSF amino acid sequence |

The following abbreviations, as used throughout the specification, are defined herein as follows:
IVF In vitro Fertilization
OHSS Ovarian Hyperstimulation Syndrome
IVM In vitro Maturation
IVP In vitro Production
MOET Multiple Ovulation and Embryo Transfer
GM-CSF Granulocyte Macrophage-Colony Stimulating Factor
HSA Human Serum Albumin
ITS Insulin-Transferrin-Selenium
IGF-1 Insulin-Like Growth Factor-1
EGF Epidermal Growth Factor
FSH Follicle Stimulating Hormone
HCG Human Chorionic Gonadotropin
LH Luteinizing Hormone
PMSG Pregnant Mare's Serum Gonadotropin
ART Assisted Reproductive Technology
ICSI Intracytoplasmic Sperm Injection
PVA Polyvinyl Alcohol As shown herein, inclusion of granulocyte macrophage-colony stimulating factor (herein referred to as "GM-CSF") in a culture medium increases the maturation and developmental competence of an oocyte cultured in the medium in vitro. With respect to assisted reproduction technologies, this allows oocytes harvested from the ovary to mature to a point close to that occurring naturally in vivo during the reproductive cycle (when compared to the maturity of oocytes collected and cultured in currently known media) prior to subsequent fertilisation of the oocyte in vitro.

Certain disclosed embodiments have one or more combinations of advantages. For example, some of the advantages of the embodiments disclosed herein include one or more of the following: culture media and methods for increasing oocyte maturation; culture media and methods for increasing developmental competence of an oocyte; culture media and methods for increasing blastocyst inner cell mass number, increasing blastocyst rate, increasing blastocyst trophectoderm cell number, increasing blastocyst total cell number, and/or increasing viability of an embryo derived from an oocyte cultured in the media; culture media and methods for decreasing DNA damage in a blastocyst derived from an oocyte cultured in the media; culture media and methods for increasing pregnancy rate following transfer of an embryo derived from an oocyte cultured in the medium to a surrogate; culture media and methods for increasing implantation of a blastocyst derived from an oocyte cultured in the medium in a surrogate; culture media and methods for increasing development to term of an embryo derived from an oocyte cultured in the medium; to provide one or more advantages, or to provide a commercial alternative. Other advantages of some embodiments of the present disclosure are provided herein.

Accordingly, in various aspects, the present invention provides an in vitro oocyte maturation medium, a medium for increasing maturation of an oocyte in vitro, and/or an in vitro culture medium when used for increasing maturation of an oocyte, the medium comprising granulocyte macrophage-colony stimulating factor (GM-CSF).

The terms "maturation medium", "medium for increasing maturation", and "in vitro culture medium" are not intended to define different media. In fact, these terms can effectively be used interchangeably and do indeed relate to the same medium, that medium comprising GM-CSF for use in oocyte maturation.

The base medium to which GM-CSF is added may be any medium which supports and maintains the viability of an oocyte cultured in the medium in vitro. A suitable base medium for example may include, but is not limited to, Tissue Culture Medium 199 (also known as Media 199, TCM199, and M199) (ThermoFisher Scientific), Minimum Essential Medium Eagle (also known as Eagles' Minimum Essential Medium, EMEM and MEM)(Sigma-Aldrich), Minimum Essential Medium Eagle Alpha Modifications (also known as α-MEM)(Sigma-Aldrich), Dulbecco's Modified Eagle Medium (also known as DMEM or D-MEM)(ThermoFisher Scientific), Ham's F12 (also known as F-12 Ham, Ham's F12 Medium, and F12 Nutrient Mixture)(ThermoFisher Scientific), RPMI Medium 1640 (ThermoFisher Scientific), Isocove's Modified Dulbecco's Medium (also known as IMDM)(ThermoFisher Scientific), Waymouth's MB 752/1 Medium (also known as Waymouth or Waymouth Medium)(Sigma-Aldrich), Chang's Medium (Irvine Scientific), HTF Medium (Irvine Scientific), Dulbecco's Modified Eagle's Medium/Nutrient F-12 Ham (also known as DMEM/F-12 and DME F12)(ThermoFisher Scientific), Vitromat (IVF Vet Solutions, Robinson Research Institute, University of Adelaide, SA, Australia) and ART-1600-B (Origio, Denmark).

With respect to the in vitro maturation of human oocytes, companies such as Origio (Denmark) provide appropriate base media. For example, GM-CSF may be added to the ART-1600-B medium supplied by Origio.

Despite the inclusion of the list above, other base media are contemplated, as would be understood by a person skilled in the art, provided that the base media supports and maintains the viability of an oocyte cultured in the medium in vitro.

ISBN 978-1-107-61953-1. Examples of additional components include, but are not limited to, inorganic ions (such as cations and anions—$Na^+$, $K^+$, $Mg^{2+}$, $Ca^{2+}$, $Cl^-$, $SO_4^{2-}$, $PO_4^{2-}$, $HCO_3^-$), energy substrates (such as glucose, lactate, pyruvate, amino acids), nitrogen sources (such as essential and non-essential amino acids), vitamins, fatty acids or precursors, nucleic acid precursors, chelators (such as EDTA), antioxidants, proteins or macromolecules (such as HSA and hyaluronate), other growth factors or hormones (such as insulin-transferrin-selenium, insulin-like growth factor, epidermal growth factor, follicle stimulating hormone and human chorionic gonadotropin), buffers to maintain a physiological pH, antibiotics, pH indicators, and combinations of any one or more of the above. It is to be made clear that certain base media may already contain one or more of the additional components listed above.

Preferred amounts and ranges of these additional components can be found in standard text books known in the art. For example, see Culture Media, Solutions, and Systems in Human ART (2014, supra), and Textbook of Assisted Reproduction: Laboratory and Clinical Perspectives (2003) Editors Gardner, D. K., Weissman, A., Howles, C. M., Shoham, Z. Martin Dunits Ltd, London, UK; and Gordon, I. (2003) Laboratory Production of Cattle Embryos 2nd Edition CABI Publishing, Oxon, UK.

For example, the maturation medium of the present invention may include one or more of the following components in the concentration ranges indicated:

| | | | |
|---|---|---|---|
| NaCl | 80.0-100 mM | KCl | 3.5-7.5 mM |
| $NaH_2PO_4 \cdot 2H_2O$ | 0.05-1.5 mM | $MgSO_4 \cdot 7H_2O$ | 0.2-4.0 mM |
| $NaHCO_3$ | 15-30 mM | $CaCl_2 \cdot 2H_2O$ | 0.8-2.8 mM |
| Glucose | 0.5-5.5 mM | NaLactate | 2.0-20 mM |
| NaPyruvate | 0.01-5.0 mM | Alanine | 0.01-1.0 mM |
| Aspartate | 0.01-1.0 mM | Asparagine | 0.01-1.0 mM |
| L-Glutamine | 0.01-1.0 mM | Alanyl-Glutamine | 0.01-2.0 mM |
| Glycine | 0.01-1.0 mM | Proline | 0.01-1.0 mM |
| Serine | 0.01-1.0 mM | Cysteamine | 0.1-2.0 mM |
| L-Arginine-HCl | 0.1-1.2 mM | L-Cystine 2HCl | 0.05-0.25 mM |
| L-Histidine-HCl—$H_2O$ | 0.1-0.4 mM | L-Isoleucine | 0.1-0.8 mM |
| L-Leucine | 0.1-0.8 mM | L-Lysine-HCl | 0.1-0.8 mM |
| L-Methionine | 0.05-0.25 mM | L-Phenylalanine | 0.1-0.4 mM |
| L-Threonine | 0.1-0.8 mM | L-Tryptophan | 0.1-0.9 mM |
| L-Tyrosine 2Na | 0.1-0.4 mM | L-Valine | 0.1-0.8 mM |
| D-Ca Pantotherate | 0.001-0.004 mM | Choline Chloride | 0.003-0.01 mM |
| Folic Acid | 0.001-0.0045 mM | i-Inositol | 0.005-0.02 mM |
| Niacinamide | 0.004-0.016 mM | Pyridoxal HCl | 0.002-0.01 mM |
| D-Pantothenic acid | 0.004-0.016 mM | Riboflavin | 0.0001-0.0006 mM |
| Thiamin HCl | 0.001-0.006 mM | HSA | 1-10.0 mg/ml |
| Hyaluronate | 0.05-0.5 mg/ml | ITS | 1-100 ng/ml |
| IGF-1 | 10-1000 ng/ml | EGF | 1-500 ng/ml |
| FSH | 0.001-10 U/ml | HCG | 1-100 U/ml |
| LH | 0.01-10 U/ml | Penicillin | 5.0-500 µg/ml |
| Streptomycin | 5.0-500 µg/ml | Gentamicin | 0.1-10.0 µg/ml |
| Insulin | 0.1-10.0 µg/ml | PMSG | 1-100 U/ml |
| Follicular fluid | 1-20% v/v | Phenol red Na | 0.001-0.1 mg/ml |
| PVA | 1-10 mg/ml | Fetuin | 0.1-10 mg/ml |
| BSA | 1-10 mg/ml | | |

The base medium to which GM-CSF is added may also be supplemented with additional components. For example, see Culture Media, Solutions, and Systems in Human ART (2014), Editor Patrick Quinn, Cambridge University Press, With respect to the maturation of human oocytes, a suitable maturation medium according to an embodiment of the present invention may include the following components in the amounts indicated:

| | | | |
|---|---|---|---|
| NaCl | 6.8 mg/ml | KCl | 400 µg/ml |
| $NaH_2PO_4$ | 122 µg/ml | $MgSO_4 \cdot 6H_2O$ | 97.67 µg/ml |
| $NaHCO_3$ | 2.2 mg/ml | $CaCl_2 \cdot 2H_2O$ | 265 µg/ml |

-continued

| | | | |
|---|---|---|---|
| Glucose | 1.0 mg/ml | L-Glutamine | 292 µg/ml |
| L-Arginine-HCl | 126 µg/ml | L-Cystine-HCl—H₂O | 31.3 µg/ml |
| L-Histidine-HCl—H₂O | 42 µg/ml | L-Isoleucine | 52 µg/ml |
| L-Leucine | 52 µg/ml | L-Lysine-HCl | 72.5 µg/ml |
| L-Methionine | 15 µg/ml | L-Phenylalanine | 32 µg/ml |
| L-Threonine | 48 µg/ml | L-Tryptophan | 10 µg/ml |
| L-Tyrosine 2Na | 51.9 µg/ml | L-Valine | 46 µg/ml |
| Choline Chloride | 1.0 µg/ml | Folic Acid | 1.0 µg/ml |
| i-Inositol | 2.0 µg/ml | Niacinamide | 1.0 µg/ml |
| Pyridoxal HCl | 1.0 µg/ml | D-Pantothenic acid | 1.0 µg/ml |
| Riboflavin | 0.1 µg/ml | Thiamin HCl | 1.0 µg/ml |
| Phenol red Na | 11 µg/ml | | |

In some embodiments, the aforementioned maturation medium with respect to human oocytes may also include one or more antibiotics such as gentamicin, penicillin and streptomycin.

In some embodiments, the base medium is M199. In some embodiments, the base medium is supplemented with pyruvate, penicillin, streptomycin sulphate, L-glutamine, cysteamine, insulin, pregnant mare's serum gonadotropin (PMSG), human chorionic gonadotropin (HCG), epidermal growth factor (EGF) and follicular fluid. For example, this medium could be used for the in vitro maturation of a porcine oocyte given that most porcine IVM media include 10 to 20% follicular fluid. Follicular fluid may therefore be an optional constituent of the maturation medium when culturing oocytes from species other than pigs.

GM-CSF is a small secreted glycoprotein that folds into a bundled structure of four antiparallel α-helices. GM-CSF is produced by many cell types, including myeloid cells, dendritic cells (DCs), T cells, B cells, and non-haematopoietic cells (such as endothelial cells, fibroblast-like synoviocytes, chondrocytes, pulmonary epithelial cells). GM-CSF is also produced by cells of the reproductive tract (namely cells of the oviduct and endometrium).

The GM-CSF protein has a number of functions, primarily acting as a cytokine stimulating stem cells to produce granulocytes and monocytes. GM-CSF also plays a role in embryonic development, where it has been localized in the granulosa at protein and mRNA levels with concentrations being higher in the follicular fluid than in the serum. GM-CSF appears to be an essential local modulator implicated in the embryo implantation process given that neutralizing GM-CSF increases spontaneous abortion.

The implication of GM-CSF in embryo development and fetal survival was first described in mice. At an embryonic level, murine blastomere viability is enhanced by GM-CSF. It also promotes embryo development in the pig, sheep and cow, particularly by increasing $IFN_T$ secretion in the latter two. GM-CSF has also been shown to have a positive trophic effect on human embryos. In this regard, the cellular mechanism implicated in this embryonic effect, by supplementing embryo culture media with human recombinant GM-CSF, is blastomere protection against apoptosis with no apparent effect on embryonic chromosomal constitution. However, a positive effect of GM-CSF on oocyte viability, maturity and developmental competence has not previously been reported.

To date, GM-CSF has been found in ninety three different mammalian species, including human, mouse, rat, cow, dog, pig, Rhesus monkey, sheep, chimpanzee, horse, cat, goat, fox, ferret, yak, macaque, cheetah, lemur, camel, bison, bear, opossum, dolphin, whale, tiger, seal, gorilla, elephant, panda, orangutan, rabbit, baboon and rhinoceros, amongst many others. GM-CSF is also referred to in the art as colony stimulating factor 2, CSF2, molgramostin and sargramostim.

GM-CSF for use in the present invention can be sourced a number of ways. For example, GM-CSF may be purchased commercially from available suppliers, including Sigma-Aldrich, ThermoFisher Scientific, Peprotech, Miltenyi Biotech, Kingfisher, Biotech, Inc., Bio-Rad, and others. In this regard, these suppliers provide GM-CSF in a purified form.

Typically, the GM-CSF is produced recombinantly in a non-human or non-animal host, such as *E. coli*. Techniques for recombinant production of proteins (including GM-CSF) and their purification are standard in the art. See, for example, Green M R and Sambrook J, *Molecular Cloning: A Laboratory Manual* (4th edition), Cold Spring Harbor Laboratory Press, 2012.

For recombinant production of GM-CSF, knowledge of the sequence of the GM-CSF gene in the desired species and encoded protein is required. In this regard, gene information may be accessed from the GenBank database at the National Center for Biotechnology Information (NCBI) (www.ncbi.nlm.nih.gov). For example, the Gene ID number for human GM-CSF is 1437. The human GM-CSF gene is represented by GenBank Accession Number NM_000758.3 (nucleotide sequence as represented by SEQ ID NO: 1) and NP_000749.2 (amino acid sequence as represented by SEQ ID NO: 2). Further details of the GM-CSF gene in other species may be accessed from the NCBI. For example, the Gene ID number for bovine GM-CSF is 281095, for pig is 397208, for horse is 100033981, for dog is 403923, for cat is 101094153, for mouse is 12981, and for sheep is 443400. The nucleotide and amino acid sequences of these species are represented by SEQ ID NOs: 3 to 16, respectively.

Details regarding the GM-CSF gene in humans and other species can also be found at the UniGene portal of the NCBI (UniGene Hs. 1349—https://www.ncbi.nlm.nih.gov/UniGene/clust.cgi?UGID=130983&TAXI D=9606&SEARCH=). Alternatively, details of the nucleotide and amino acid sequence for GM-CSF can be accessed from the UniProt database (www.uniprot.org) wherein the UniProt ID for human GM-CSF is P04141.

It is to be made clear that reference herein to GM-CSF includes a reference to variants thereof. In this regard, a "variant" of GM-CSF may exhibit a nucleic acid or an amino acid sequence that is at least 80% identical, at least 90% identical, at least 95% identical, at least 98% identical, at least 99% identical, or at least 99.9% identical to native GM-CSF provided that the variant retains biological activity, or a substantial equivalent thereof, of the native GM-CSF. Such a variant of GM-CSF may be referred to as a "functionally active variant". Other levels of identity are contemplated, including variants with less than 80% identity.

A functionally active variant of GM-CSF may comprise individual amino acid substitutions, deletions or insertions relative to the native GM-CSF sequence (for example SEQ ID NO: 2 with respect to human GM-CSF). For example, a person skilled in the art will recognise that any amino acid can be substituted with a chemically (functionally) similar amino acid and retain function of the polypeptide. Such conservative amino acid substitutions are well known in the art. The following groups in Table 2 each contain amino acids that are conservative substitutions for one another.

TABLE 2

Exemplary amino acid conservative substitutions

| Original Residue | Exemplary Substitutions |
|---|---|
| Ala (A) | Val (V), Leu (L), Ile (I), Gly (G) |
| Arg (R) | Lys (K) |
| Asn (N) | Gln (Q), His (H) |
| Asp (D) | Glu (E) |
| Cys (C) | Ser (S) |
| Gln (Q) | Asn (N), His (H) |
| Glu (E) | Asp (D) |
| Gly (G) | Pro (P), Ala (A) |
| His (H) | Asn (N), Gln (Q) |
| Ile (I) | Leu (L), Val (V), Ala (A) |
| Leu (L) | Ile (I), Val (V), Met (M), Ala (A), Phe (F) |
| Lys (K) | Arg (R) |
| Met (M) | Leu (L), Phe (F) |
| Phe (F) | Leu (L), Val (V), Ala (A) |
| Pro (P) | Gly (G) |
| Ser (S) | Thr (T) |
| Thr (T) | Ser (S) |
| Trp (W) | Tyr (Y) |
| Tyr (Y) | Trp (W), Phe (F) |
| Val (V) | Ile (I), Leu (L), Met (M), Phe (F), Ala (A) |

Furthermore, if desired, unnatural amino acids or chemical amino acid analogues can be introduced as a substitution or addition into a polypeptide encompassed herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexyl-alanine, β-alanine, fluoro-amino acids, designer amino acids such as β-methyl amino acids, Cα-methyl amino acids, Nα-methyl amino acids, and amino acid analogues in general.

When comparing amino acid sequences to define a variant of GM-CSF, the native and variant sequences should be compared over a comparison window which is determined by the length of the polypeptide. For example, a comparison window of at least 20 amino acid residues, at least 50 amino acid residues, at least 75 amino acid residues, at least 100 amino acid residues, or over the full length of the native GM-CSF is envisaged. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as, for example, disclosed by Altschul et al., 1997, *Nucl. Acids Res.* 25: 3389-3402. Global alignment programs may also be used to align similar sequences of roughly equal size. Examples of global alignment programs include NEEDLE (available at www.ebi.ac.uk/Tools/psa/emboss_needle/) which is part of the EMBOSS package (Rice P et al., 2000, *Trends Genet.*, 16: 276-277), and the GGSEARCH program (available at fasta.bioch.virginia.edu/fasta_www2/fasta_www.cgi?rm=compare&pgm=gnw) which is part of the FASTA package (Pearson W and Lipman D, 1988, *Proc. Natl. Acad. Sci. USA*, 85: 2444-2448). Both of these programs are based on the Needleman-Wunsch algorithm which is used to find the optimum alignment (including gaps) of two sequences along their entire length. A detailed discussion of sequence analysis can also be found in Unit 19.3 of Ausubel et al ("Current Protocols in Molecular Biology" John Wiley & Sons Inc, 1994-1998, Chapter 15, 1998).

The amount of GM-CSF present in the medium is generally in the range of about 0.1 ng/ml to about 100 ng/ml. For example, the GM-CSF may be present in an amount from about 0.1 to about 90 ng/ml, about 0.1 to about 80 ng/ml, about 0.1 to about 70 ng/ml, about 0.1 to about 60 ng/ml, about 0.1 to about 50 ng/ml, about 0.1 to about 40 ng/ml, about 0.1 to about 30 ng/ml, about 0.1 to about 20 ng/ml, about 0.1 to about 10 ng/ml, about 0.1 to about 5.0 ng/ml, about 0.1 to about 4.0 ng/ml, about 0.1 to about 3.0 ng/ml, about 0.1 to about 2.0 ng/ml, about 0.1 to about 1.0 ng/ml, about 0.1 to about 0.5 ng/ml, about 0.5 to about 100 ng/ml, about 0.5 to about 90 ng/ml, about 0.5 to about 80 ng/ml, about 0.5 to about 70 ng/ml, about 0.5 to about 60 ng/ml, about 0.5 to about 50 ng/ml, about 0.5 to about 40 ng/ml, about 0.5 to about 30 ng/ml, about 0.5 to about 20 ng/ml, about 0.5 to about 10 ng/ml, about 0.5 to about 5.0 ng/ml, about 0.5 to about 4.0 ng/ml, about 0.5 to about 3.0 ng/ml, about 0.5 to about 2.0 ng/ml, about 0.5 to about 1.0 ng/ml, about 1.0 to about 100 ng/ml, about 1.0 to about 90 ng/ml, about 1.0 to about 80 ng/ml, about 1.0 to about 70 ng/ml, about 1.0 to about 60 ng/ml, about 1.0 to about 50 ng/ml, about 1.0 to about 40 ng/ml, about 1.0 to about 30 ng/ml, about 1.0 to about 20 ng/ml, about 1.0 to about 10 ng/ml, about 1.0 to about 9.0 ng/ml, about 1.0 to about 8.0 ng/ml, about 1.0 to about 7.0 ng/ml, about 1.0 to about 6.0 ng/ml, about 1.0 to about 5.0 ng/ml, about 1.0 to about 4.0 ng/ml, about 1.0 to about 3.0 ng/ml, and about 1.0 to about 2.0 ng/ml.

In some embodiments, the GM-CSF may be present in the medium in the range of about 2.0 ng/ml to about 10 ng/ml. For example, the GM-CSF may be present in an amount from about 2.0 ng/ml to about 9.0 ng/ml, about 2.0 ng/ml to about 8.0 ng/ml, about 2.0 ng/ml to about 7.0 ng/ml, about 2.0 ng/ml to about 6.0 ng/ml, about 2.0 ng/ml to about 5.0 ng/ml, about 2.0 ng/ml to about 4.0 ng/ml, about 2.0 ng/ml to about 3.0 ng/ml, about 3.0 ng/ml to about 10 ng/ml, about 3.0 ng/ml to about 9.0 ng/ml, about 3.0 ng/ml to about 8.0 ng/ml, about 3.0 ng/ml to about 7.0 ng/ml, about 3.0 ng/ml to about 6.0 ng/ml, about 3.0 ng/ml to about 5.0 ng/ml, about 3.0 ng/ml to about 4.0 ng/ml, about 4.0 ng/ml to about 10 ng/ml, about 4.0 ng/ml to about 9.0 ng/ml, about 4.0 ng/ml to about 8.0 ng/ml, about 4.0 ng/ml to about 7.0 ng/ml, about 4.0 ng/ml to about 6.0 ng/ml, about 4.0 ng/ml to about 5.0 ng/ml, about 5.0 ng/ml to about 10 ng/ml, about 5.0 ng/ml to about 9.0 ng/ml, about 5.0 ng/ml to about 8.0 ng/ml, about 5.0 ng/ml to about 7.0 ng/ml, about 5.0 ng/ml to about 6.0 ng/ml, about 6.0 ng/ml to about 10 ng/ml, about 6.0 ng/ml to about 9.0 ng/ml, about 6.0 ng/ml to about 8.0 ng/ml, about 6.0 ng/ml to about 7.0 ng/ml, about 7.0 ng/ml to about 10 ng/ml, about 7.0 ng/ml to about 9.0 ng/ml, about 7.0 ng/ml to about 8.0 ng/ml, about 8.0 ng/ml to about 10 ng/ml, about 8.0 ng/ml to about 9.0 ng/ml, and about 9.0 ng/ml to about 10 ng/ml.

In some embodiments, the amount of GM-CSF present in the medium may be about 2 ng/ml.

In some embodiments, the amount of GM-CSF present in the medium may be about 10 ng/ml.

The medium of the present invention may be used to mature an oocyte obtained from any mammalian origin. In some embodiments, the oocyte is selected from the group consisting of a human oocyte, a bovine oocyte, a porcine oocyte, an equine oocyte, a canine oocyte, a feline oocyte, a murine oocyte (e.g. mouse and rat), an ovine oocyte, and a non-human primate oocyte.

The subject from which the oocyte is obtained may be an otherwise healthy subject but for their reduced capacity or inability to conceive and/or carry a pregnancy to term. Alternatively, the subject may be aged and/or obese thereby also having a reduced capacity or inability to conceive and/or carry a pregnancy to term due to the effect of age and/or obesity on oocyte developmental competence. An aged subject would be considered a subject who is older than the peak fertility age range of the particular species. For an otherwise healthy human subject that range is between the ages of 23 and 35. Therefore an aged human subject could be considered a subject older than 35. Of course the peak fertility age range in humans may vary depending on a number of factors, including race, ethnicity, and genetic background.

In some embodiments, the GM-CSF for inclusion in the medium is species-specific. That is, the source of the GM-CSF is the same as the source of the oocyte. For example, the GM-CSF may be recombinant or native human GM-CSF and the oocyte is a human oocyte. Alternatively, the GM-CSF may be recombinant or native porcine GM-CSF and the oocyte is a porcine oocyte.

Accordingly, in some embodiments, the oocyte is a porcine oocyte, the GM-CSF is porcine GM-CSF and the amount of porcine GM-CSF present in the medium may be about 2 ng/ml.

In some embodiments, the oocyte is a porcine oocyte, the GM-CSF is porcine GM-CSF and the amount of porcine GM-CSF present in the medium may be about 10 ng/ml.

In some embodiments, the oocyte is a bovine oocyte, the GM-CSF is bovine GM-CSF and the amount of bovine GM-CSF present in the medium may be about 2 ng/ml.

In some embodiments, the oocyte is a bovine oocyte, the GM-CSF is bovine GM-CSF and the amount of bovine GM-CSF present in the medium may be about 10 ng/ml.

In some embodiments, the oocyte is a murine oocyte, the GM-CSF is murine GM-CSF and the amount of murine GM-CSF present in the medium may be about 2 ng/ml.

In some embodiments, the oocyte is a murine oocyte, the GM-CSF is murine GM-CSF and the amount of murine GM-CSF present in the medium may be about 10 ng/ml.

In some embodiments, the oocyte is a human oocyte, the GM-CSF is human GM-CSF and the amount of human GM-CSF present in the medium may be about 2 ng/ml.

In some embodiments, the oocyte is a human oocyte, the GM-CSF is human GM-CSF and the amount of human GM-CSF present in the medium may be about 10 ng/ml.

Throughout the specification, reference to an oocyte encompasses an oocyte devoid of companion cells, or inclusive of companion cells. For example, the oocyte may be a denuded oocyte wherein the somatic cell layers (e.g. cumulus cells) that surround the oocyte have been removed. The oocyte may also be part of a follicle, or may be part of a cumulus oocyte complex (COC) in which the cumulus vestments remain intact.

As indicated above, it has been determined that maturation of oocytes harvested from the ovary is increased when the harvested oocyte is cultured in a medium comprising GM-CSF. In this regard, the success of assisted reproductive technologies depends to a large extent on the maturity of the oocyte prior to fertilization. Oocytes harvested from ovaries typically undergo spontaneous resumption of meiosis, i.e. proceed in their nuclear maturation, when placed in culture. This nuclear maturation may often occur before the oocyte has undergone other aspects of maturity, such as cytoplasmic maturity. An immature oocyte may ultimately affect the success of fertilization and possibly subsequent embryo implantation and development.

Indeed, the inventor has found that inclusion of GM-CSF in culture media for an oocyte, while increasing the maturity of the oocyte, also increases developmental competence of the oocyte. In this regard, the term "developmental competence" is to be understood to mean the capacity of the oocyte to develop into an embryo capable of implanting, developing to term and producing healthy offspring.

An "increase" in maturation and an "increase" in developmental competence is meant to refer to a level of maturity and developmental competence of the oocyte that is greater than that of an oocyte of the same species or from the same animal when cultured in a base medium which does not comprise GM-CSF. For example, the maturation and developmental competence of the oocyte cultured in a medium comprising GM-CSF may be increased by at least 5%, 10%, 20%, 30%, 40%, 50%, 60%, 70%, 80%, 90%, 100% or greater, 2-fold, 5-fold, 10-fold, 20 fold, 50-fold, or 100-fold or greater, relative to a control "untreated" oocyte.

An increase in maturation and developmental competence may be assayed a number of ways. Ultimately, the most appropriate assays will evaluate positive effects on indicators of embryo viability and quality following fertilization of the "matured" oocyte.

Suitable assays for example may examine for increased blastocyst inner cell mass number, increased blastocyst rate/number of blastocysts (measured for example by the number of oocytes that develop to the blastocyst stage after fertilization, and/or the number of oocytes that reach the blastocyst stage at the same time/rate as that would occur in vivo following normal/natural fertilization), increased trophectoderm cell number, increased total blastocyst cell number (the number of inner cell mass cells plus the number of trophectoderm cells), increased cleavage (measured for example by the ability of an oocyte to fertilize and divide to the two-cell stage), embryo morphology, number of blastocysts that hatch, pregnancy rate (measured for example by the success of pregnancy in a surrogate following transfer of an embryo derived from an oocyte cultured in a medium comprising GM-CSF, and/or by the number of horns which had implantations/fetuses present), and examination of DNA damage in a blastocyst or gene expression patterns. Alternatively, an appropriate assay will simply evaluate for an improvement in embryo viability following fertilization of the "matured" oocyte compared to known industry standards, or will test for the ability of the treated oocyte to develop into an embryo capable of implanting or developing to term (i.e. a birth), as indicated above. Other assays would be known to a person skilled in the art.

With respect to an "increased blastocyst inner cell mass number", "increased blastocyst rate", "increased blastocyst trophectoderm cell number", "increased blastocyst total cell number", "increased cleavage", and "increased viability", the level of increase of each parameter compared to a relevant control (for example an embryo/blastocyst derived from an oocyte of the same species or from the same animal but which has not been exposed to GM-CSF, for example an oocyte cultured in a base medium which does not comprise GM-CSF) is taken to include at least a 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 70%, 80%, 90%, 100%, 105%, 110%, 120%, 130%, 140%, 150%, 160%, 170%, 180%, 190%, 200%, 210%, 220%, 230%, 240%, 250% or greater, 2-fold, 5-fold, 10-fold, 20 fold, 50-fold, or 100-fold or greater, increase.

Similarly, an "increased pregnancy rate", "increased implantation" and "increased development to term" means an increase in the relevant parameter compared to a relevant control (for example an embryo/blastocyst which is derived from an oocyte of the same species or from the same animal but which has not been exposed to GM-CSF, for example an oocyte cultured in a base medium which does not comprise GM-CSF). That increase may be at least a 5%, 10%, 15%, 20%, 25%, 30%, 35%, 40%, 45%, 50%, 55%, 60%, 65% 70%, 75%, 80%, 85%, 90%, 95%, 100%, 105%, 110%, 120%, 130%, 140%, 150%, 160%, 170%, 180%, 190% or greater, 2-fold, 5-fold, 10-fold, 20 fold, 50-fold, or 100-fold or greater compared to the control.

Finally, a "decrease" in DNA damage in a blastocyst means a level of damage that is less than that of a blastocyst derived from an oocyte of the same species or from the same animal when cultured in a base medium which does not comprise GM-CSF. A decrease in DNA damage is reflective of the ability of the oocyte maturation medium to reduce the environmental stress associated with in vitro culture of the oocyte. That decrease may be at least a 5%, 6%, 7%, 8%, 9%, 10%, 20%, 30%, 40%, 50%, 60%, 70%, 80%, 90%, 100%, 105%, 110%, 120%, 130%, 140%, 150%, 160%, 170%, 180%, 190% or less, 2-fold, 5-fold, 10-fold, 20 fold, 50-fold, or 100-fold or less, compared to the control.

As used herein, the term "derived from" includes an embryo which has been produced by in vitro fertilization of an oocyte.

An oocyte can be harvested or collected from an ovary according to standard techniques long known in the art. For example, see Textbook of Assisted Reproduction: Laboratory and Clinical Perspectives (2003, supra). Most oocyte collection techniques involve the insertion of an aspirating needle into an ovarian follicle using transvaginal ultrasound. The aspirating needle is connected by tubing to a material collection trap and the collection trap, in turn, is connected to a suction source such as a manually operated syringe or an electromechanical vacuum source. Oocytes are typically isolated from multiple follicles. As such, harvested oocytes represent a heterogeneous population with regard to their maturity and therefore developmental potential.

As will be appreciated, the time for maturation of the oocyte in the medium of the present invention may differ between species. Generally the time for maturation will be the time that the meiotic stage of metaphase II is reached in these systems, and as such the time for maturation will typically be from 6 hours to 44 hours for the oocyte to reach the metaphase II stage of meiosis. For example in the bovine setting the IVM time will generally be in the range from 18-24 hours in the absence of GM-CSF in the medium. In the human setting, the IVM time will generally be about 28 to about 52 hours, and most usually between about 30 to about 36 hours in the absence of GM-CSF in the medium.

In one embodiment, the oocyte is a porcine oocyte and the porcine oocyte is cultured in the medium of the present invention for about 40 to 42 hours at 35-39° C. with a suitable gas mixture prior to fertilisation. An example of a suitable gas mixture includes, but is not limited to, a gas mixture comprising of $CO_2$ (1-10% by volume), balanced with air or with mixtures of $O_2$ and $N_2$ in proportions that sustain biological activity. For example, with respect to human oocytes incubation is typically at 37° C. in an incubator with an atmosphere of 5% $CO_2$ and 95% air with high humidity (or with triple gas mixture (90% $N_2$, 5% $CO_2$, and 5% $O_2$) and 100% humidity).

In a further aspect, by establishing that inclusion of GM-CSF in a culture medium increases the maturation of an oocyte cultured in the medium in vitro, the present invention provides a method of in vitro maturation of an oocyte, the method comprising culturing the oocyte in a maturation medium as described above.

In a further aspect, the present invention also provides a method for increasing maturation of an oocyte in vitro, the method comprising culturing the oocyte in a medium comprising GM-CSF.

Given that presence of GM-CSF in the medium also increases developmental competence of the oocyte, in a further aspect the present invention provides a method of increasing developmental competence of an oocyte in vitro, the method comprising culturing the oocyte in a medium comprising GM-CSF.

In this regard, in a further aspect there is also provided an isolated oocyte with increased maturation and increased developmental competence produced by the aforementioned methods, and an embryo or non-human animal produced from the oocyte.

The oocyte with increased maturation and increased developmental competence produced by the aforementioned methods in vitro may form part of an assisted reproductive technology. The term "assisted reproductive technology" as used throughout the specification is to be understood to mean any laboratory or clinical technology applied to isolated gametes (oocytes or sperm) and/or embryos for the purposes on reproduction.

Such technologies include in vitro fertilization (IVF; aspiration of an oocyte, fertilization in the laboratory and transfer of the embryo into a recipient), gamete intrafallopian transfer (GIFT; placement of oocytes and sperm into the fallopian tube), zygote intrafallopian transfer (ZIFT; placement of fertilized oocytes into the fallopian tube), tubal embryo transfer (TET; the placement of cleaving embryos into the fallopian tube), peritoneal oocyte and sperm transfer (POST; the placement of oocytes and sperm into the pelvic cavity), intracytoplasmic sperm injection (ICSI), testicular sperm extraction (TESE), and microsurgical epididymal sperm aspiration (MESA); or any other in vitro technique for producing embryos in humans and/or animals, such as nuclear transfer, parthenogenic activation, embryonic stem cell production, and the use of totipotent cells.

In one embodiment, the assisted reproductive technology comprises in vitro fertilization (IVF). IVF relates to the fertilization of an oocyte in vitro, wherein the oocyte is isolated from the subject and incubated in media to allow fertilization of the oocyte. As indicated above, methods are well known in the art for collecting oocytes from suitable females and fertilizing the oocytes in vitro. It is contemplated that fertilization of the oocyte will ideally occur no less than 24 hours, but no later than 60 hours, after collection of the oocyte and culturing in the medium of the present invention, such that maturity of the oocyte is at a sufficient stage to maximize the success of subsequent steps in the IVF procedure. For in vitro fertilization, the sperm may be incubated with the matured oocyte for a period of between 1 to 60 hours.

Accordingly, in a further aspect, the present invention provides a method of producing an embryo from an oocyte by an assisted reproductive technology, the method comprising:
(a) collecting an oocyte from an ovary of a subject;
(b) culturing the oocyte in vitro in a medium comprising GM-CSF; and
(c) producing an embryo from the oocyte by fertilisation of the oocyte in vitro.

In a further aspect, the present invention provides a method of assisted reproduction involving an oocyte, the method comprising the step of exposing the oocyte to GM-CSF in vitro. In a still further aspect, there is provided a method of assisted reproduction involving an oocyte, the method comprising the step of in vitro maturation of an oocyte by exposing the oocyte to GM-CSF in vitro. In some embodiments, the methods comprise the further step of exposing an embryo derived from the oocyte to GM-CSF in vitro.

In some embodiments, the assisted reproductive technology or the method of assisted reproduction is in vitro fertilisation.

In circumstances where it is desired to accomplish fertilisation by other than natural interaction of sperm and oocyte, such as where the sperm is unable to fertilise the oocyte due to a thickened zona pellucida surrounding the oocyte, or where the sperm is from a male-factor patient, the sperm may be transported into the oocyte by a technique called intracytoplasmic sperm injection (ICSI). Accordingly, in some embodiments, the assisted reproductive technology or the method of assisted reproduction is ICSI. When the ICSI technique is used, the cumulus cells are removed from the oocyte, and sperm is injected into the interior of the oocyte using a glass pipette.

With respect to any of the aforementioned assisted reproductive technologies, the collected sperm may be maintained in a medium prior to fertilisation. A suitable medium would be known in the art and is set out in standard texts, such as the Textbook of Assisted Reproduction: Laboratory and Clinical Perspectives (2003, supra). The medium containing the sperm may be of a constitution so as to minimise any stress placed on the oocyte when transferred from the maturation medium of the present invention to the medium containing the sperm. Accordingly, in some embodiments the medium housing the sperm may have a similar or identical composition of ions and non-essential amino acids as the maturation medium.

In some embodiments, the medium containing the sperm may comprise GM-CSF.

With respect to the fertilization process, a suitable medium in which this is conducted (i.e. a fertilization medium) would be known in the art and is set out in standard texts, such as the Textbook of Assisted Reproduction: Laboratory and Clinical Perspectives (2003, supra). The fertilization medium may be of a constitution so as to promote sperm function and fertilization. For example, the fertilization medium may comprise an elevated concentration of sodium and/or phosphate compared to the maturation medium of the present invention. The fertilization medium may also be supplemented with the carbohydrates glucose, lactate and pyruvate. Specific formulations may involve supplementation of the medium with one or more of bicarbonate, glutathione to promote sperm head decondensation, non-essential amino acids, HSA, hyaluronate, and antibiotics such as penicillin and streptomycin.

In some embodiments, the fertilization medium may comprise GM-CSF.

Alternatively, the collected sperm may be transferred directly into the maturation medium of the present invention which contains the matured oocyte (for in vitro fertilisation) or may be injected directly into a matured oocyte that is present in the maturation medium (for ICSI).

With respect to the ICSI technique, an alternative arrangement would be to use a single medium (an ICSI medium) that can be used to culture the matured oocyte and can also serve as a carrier for the sperm as it is transported by injection into the oocyte. The ICSI medium should preferably be highly compatible with the interior and exterior of the matured oocyte. The ICSI media may be a base medium as described above and may comprise ionic constituents similar to those found in the oocyte maturation medium of the present invention. In one embodiment, phosphate may be omitted to avoid metabolic and homeostatic stress on the matured oocyte. Because ICSI is a clinical procedure performed outside the incubator, a buffering system that is effective in a normal atmosphere is typically used. MOPS and HEPES are accordingly preferred buffers for the ICSI medium. Because the cumulus cells have been removed from the oocyte, and the sperm is at the conclusion of its independent life, glucose (the main energy source for cumulus cells and sperm, but not the oocyte) may be omitted from the ICSI medium. In order to nourish the matured oocyte, non-essential amino acids most abundant in the oocyte (e.g. glycine, proline, serine and taurine) and glutamine can be included in the ICSI medium to avoid osmotic and pH stress. The ICSI medium may also include hyaluronate or polyvinylpyrollidone (PVP) to immobilize or slow the sperm so that they may be captured in the ICSI pipette.

In some embodiments, the ICSI medium may comprise GM-CSF.

Following fertilisation, the embryo may be incubated in a medium which supports development of the embryo (an embryo culture medium). The embryo culture medium may be a base medium as described above and may comprise ionic constituents similar to those found in the oocyte maturation medium of the present invention. In one embodiment, the embryo culture medium may comprise EDTA which is believed to bind and disable toxins that may be deleterious to the early embryo. The embryo culture medium may also comprise HSA and hyaluronate. Furthermore, alanyl-glutamine may be substituted for glutamine to reduce ammonium build up within the medium.

In some embodiments, the embryo culture medium may comprise GM-CSF.

In some embodiments, all media in which a harvested oocyte comes into contact, including from collection of the oocyte, to fertilization of the oocyte, and to subsequent embryo culture and development, may include GM-CSF. For example, it is expected that the presence of GM-CSF in the oocyte maturation media, the presence of GM-CSF in the medium containing the sperm, the presence of GM-CSF in the fertilization medium, and the presence of GM-CSF in media containing the oocyte following fertilization, will have an additive effect on blastocyst development, pregnancy rates, and ultimately development to term.

In some embodiments of the aforementioned methods, the amount of GM-CSF present in the respective media may be that as described above. In some embodiments, the amount of GM-CSF present in the media is generally in the range of about 0.1 ng/ml to about 100 ng/ml. For example, the GM-CSF may be present in the media in the range of about 2.0 ng/ml to about 10 ng/ml.

In further aspects, the present invention provides granulocyte macrophage-colony stimulating factor (GM-CSF) for use, or when used, in a culture medium for increasing maturation of an oocyte in vitro or for increasing developmental competence of an oocyte in vitro. In another aspect, the present invention provides use of granulocyte macrophage-colony stimulating factor (GM-CSF) in the preparation of a culture medium for increasing maturation of an oocyte in vitro or for increasing developmental competence of an oocyte in vitro.

In further aspects, the present invention also allows for the preparation of a combination product for use in, or when used for, increasing maturation of an oocyte in vitro or for increasing developmental competence of an oocyte in vitro. In one aspect, a combination product may comprise:
  (i) a culture medium;
  (ii) granulocyte macrophage-colony stimulating factor (GM-CSF); and optionally
  (iii) instructions for culturing an oocyte in the culture medium comprising the GM-CSF.

In another aspect, a combination product may comprise:
  (i) a culture medium comprising granulocyte macrophage-colony stimulating factor (GM-CSF); and
  (ii) instructions for culturing an oocyte in the culture medium.

A suitable culture medium for the combination product is described above with reference to the base medium. The source of GM-CSF has also been described above and in some embodiments is species-specific. The instructions may direct the user to the amount of GM-CSF to add to the medium, and may provide conditions which can be used for incubation of an oocyte in the medium. The instructions may be in the form of a suitable label or may be a separate insert.

In some embodiments, the combination product is used as part of an assisted reproductive technology. Examples of an assisted reproductive technology are described above.

Individual oocytes (including cumulus oocyte complexes), whole follicles, ovarian tissue, or whole ovaries when frozen typically die as a result of freeze/thawing. It is envisaged that the present invention is also suitable for reducing damage to these cells/tissues due to freeze-thawing.

Accordingly, in another aspect the present invention provides a method of reducing damage to an oocyte, follicle, ovarian tissue or ovary due to freeze-thawing, the method comprising exposing the oocyte, follicle, ovarian tissue or ovary to a medium comprising granulocyte macrophage-colony stimulating factor (GM-CSF). It is envisaged that exposure to GM-CSF will lead to the oocyte maturing to a point where it can best cope with the freeze-thawing cycle.

It is to be noted that where a range of values is expressed, it will be clearly understood that this range encompasses the upper and lower limits of the range, and all values in between these limits.

The term "about" as used in the specification means approximately or nearly and in the context of a numerical value or range set forth herein is meant to encompass variations of +1-10% or less, +1-5% or less, +1-1% or less, or +1-0.1% or less of and from the numerical value or range recited or claimed.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the singular forms "a," "an," and "the" may refer to plural articles unless specifically stated otherwise.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

Furthermore, the description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

The invention is further illustrated in the following examples. The examples are for the purpose of describing particular embodiments only and are not intended to be limiting with respect to the above description. It will be appreciated by those skilled in the art that the disclosure may be embodied in many other forms.

Example 1

Effect of GM-CSF on Maturation of Porcine Oocytes In Vitro

The effect of adding granulocyte macrophage-colony stimulating factor (GM-CSF) to various oocyte maturation media was examined in pigs in dose response experiments using recombinant GM-CSF. Embryos were produced using in vitro embryo production systems. Experiments examined the number of embryos that cleaved and developed to the blastocyst stage as well as blastocyst inner cell mass, trophectoderm and total cell numbers as measures of oocyte developmental competence. All chemicals were purchased from Sigma-Aldrich unless otherwise stated.

Methods

1. Oocyte Maturation and In Vitro Embryo Production—Method 1

1.1 Oocyte Collection and In Vitro Maturation

Porcine ovaries were collected from a local abattoir and transported to the laboratory in a 0.9% sodium chloride solution at between 33° C. and 37° C. Small antral follicles between 3 to 6 mm in diameter were aspirated using a 21-gauge needle connected to a constant vacuum source. The follicular contents were pooled in collection tubes to be searched through using a dissection microscope.

Cumulus-oocyte complexes (COCs) with at least three compact cumulus layers and an evenly granulated cytoplasm were recovered from the collected fluid and pooled in a 1 ml drop of Medium 199 Hepes (M199 HEPES; Life Technologies, Vic, AUS—now ThermoFisher Scientific) with 10% sow follicular fluid under oil. Once all the collection tubes were processed the pooled COCs were washed three times through a basic maturation media. During the last wash the COCs went through a final selection process were any unsuitable COCs were removed. The remaining COCs were allocated randomly into groups of 50-60 COCs then cultured in basic maturation media supplemented with 0 ng/ml, 2 ng/ml or 10 ng/ml of porcine GM-CSF. Each treatment group was cultured in 600 µl of maturation media covered with mineral oil in the well of a 4-well nunclon IVF multidish for 40-42 hrs in an atmosphere of 5% $CO_2$ in air at 38.5° C.

The basic maturation media consisted of 50 ml of Medium 199 (M199; Life Technologies, Vic, AUS—now ThermoFisher Scientific) supplemented with 5.0 mg Na-pyruvate, 3.8 mg penicillin-G, 2.5 mg streptomycin sulphate, 5 mg L-glutamine, 5 µL cysteamine (5M stock), and the maturation working solution contained 9 ml of the basic media supplemented with 10 µl insulin (5 mg/ml stock), 100 µl PMSG (1000 iu/ml stock), 100 µl HCG (1000 iu/ml stock), 5 µl EGF (10 µg/ml stock) and 1 ml filtered sterilized sow follicular fluid. Follicular fluid was thawed and filter sterilized (Millipore, USA; filter pore size 0.22 µm) immediately prior to use.

1.2 In Vitro Fertilization (IVF) and In Vitro Culture (IVC)

After maturation, the COCs were co-incubated with mixed boar semen (Landrace/Large White) for 6 h in an atmosphere of 5% $CO_2$ in air at 38.5° C. Fertilization was performed in 100 µl droplets of TALP-PVA fertilization medium under mineral oil (Bavister B D, 1989, A consistently successful procedure for in vitro fertilization of golden hamster eggs, *Gamete Research*, 23(2): 139-158). TALP-PVA stock medium contained 114.0 mM NaCl, 3.16 mM KCl, 4.72 mM $CaCl_2.2H_2O$, 0.5 mM $MgCl_2.6H_2O$, 25 mM $NaHCO_3$, 5 mM D-Glucose, 0.075 mg/ml penicillin-G, 0.05 mg/ml streptomycin sulphate, and 1.0 mg/ml PVA and the working solution was supplemented with 10 mM Na-lactate, 0.1 mM Na-pyruvate, 2 mM caffeine-sodium benzoate, 3 mM Ca-lactate2pentahydrate and 3 mg/ml of BSA (fraction V). Sperm was prepared by centrifuging the semen twice at 1300 RPM for 5 min and washed with Sperm Pre-incubation Media composed of M199 supplemented with 5 mg Na-pyruvate, 0.9 mg/ml Ca-lactate, 0.075 mg/ml penicillin, 0.05 mg/ml streptomycin sulphate, 6 ml heat inactivated FBS and 0.1 mg/ml of L-glutamine, before diluting with TALP-PVA medium to give a final sperm concentration of $5\times10^6$ sperm/ml. 10 µl of the prepared sperm was added to 90 µl droplets of TALP-PVA medium containing the matured COCs to give a final sperm concentration of $5\times10^5$ sp/ml.

Following fertilization, the cumulus cells were removed by repetitive pipetting and the zygotes washed twice through modified NCSU-23 (NCSU-PLG) supplemented with 0.2 mM pyruvate, 5.7 mM Na-lactate, 0.6 mM glucose & MEM-nonessential amino acids (Invitrogen, USA) and then cultured in 50 µl NUSU-PLG drops under mineral oil for day's 1 to 3. On the 3rd day embryos were checked for cleavage and transferred into new drops of modified NCSU-23 (NCSU-G), supplemented with 5.5 mM glucose and MEM non-essential and essential amino acids (Invitrogen, USA) for day's 3 to 6. On the 5th day post fertilization, 10% foetal bovine serum was added to the culture drops and morphology assessed.

Embryos were cultured for 6 days in a humidified atmosphere of 5% $CO_2$, 5% $O_2$ and the balance Nitrogen at 38.5° C. Blastocyst development was determined on Day 5 and Day 6. Day 6 blastocysts were differentially stained to determine total cell number, inner cell mass number and trophectoderm cell number.

On Day 6 of embryo development blastocysts were scored based upon morphological appearance. Blastocysts were scored as being either; small, medium, expanded or hatched/hatching based upon blastocyst diameter and cavity size.

2. Oocyte Maturation and In Vitro Embryo Production—Method 2

2.1 Oocyte Collection and In Vitro Maturation

Ovaries were collected from a local abattoir and transported for 2 hrs at 37° C. to the laboratory in a 0.9% sodium chloride saline solution. In the laboratory, small antral follicles (3-6 mm in diameter) were aspirated using an 18-20 guage syringe.

Cumulus-oocyte complexes (COCs) were removed and selected based upon morphological appearance. COCs with fewer than three layers of cumulus cells, with an overly expanded and uneven or dark cumulus layer, or with abnormal nuclei, were excluded. COCs were washed once through Medium 199 HEPES (M199 HEPES; Life Technologies, Vic, AUS—now ThermoFisher Scientific) and then twice through BOMED maturation media (Kühholzer B et al., 2001, Clonal lines of transgenic fibroblast cells derived from the same fetus result in different development when used for nuclear transfer in pigs, *Biology of Reproduction*, 64(6): 1695-1698) supplemented with 3 mg/ml polyvinyl alcohol (PVA). The basic maturation media consisted of 50 ml of Medium 199 (Invitrogen, Carlsbad, Calif., USA) supplemented with 5.0 mg Na-pyruvate, 3.8 mg penicillin-G, 2.5 mg streptomycin sulphate, and 5 µl cysteamine (5 M stock). The final or working BOMED maturation media contained 10 ml of the basic maturation media supplemented with 10 µl insulin (5 mg/ml stock), 100 µl PMSG (1000 iu/ml stock, Folligon, Intervet, Castle Hill, Australia), 100 µl HCG (1000 iu/ml stock, Chorulon, Intervet, Castle Hill, Australia), 5 µl EGF (10 µg/ml stock) and 3 mg/ml PVA (Beebe L F S et al., 2007, The effect of energy substrate concentration and amino acids on the in vitro development of preimplantation porcine embryos, Cloning and Stem Cells, 9(2): 206-215). For each treatment group (0 ng/ml, 2 ng/ml or 10 ng/ml of porcine GM-CSF), 50 COCs were cultured in 600 µl of maturation media covered with mineral oil in the well of a 4-well nunclon IVF multidish for 40-42 hrs in an atmosphere of 5% $CO_2$ in air at 38.5° C.

2.2 In Vitro Fertilization (IVF) and In Vitro Culture (IVC)

After maturation, the COCs were co-incubated with mixed boar semen (Landrace/Large White; SABOR Pty Ltd Clare SA) for 6 hrs at 38.5° C. in 5% $CO_2$ air. Fertilization was performed in 100 µl droplets of TALP-fertilization medium (Bavister BD, 1989 supra) under mineral oil. TALP-fertilization medium contained 25 ml of TALP-PVA stock solution (114 mM NaCl, 3.16 mM KCl, 4.72 mM $CaCl_2.2H_2O$, 0.5 mM $MgCl_2.6H_2O$, 25 mM $NaHCO_3$, 5 mM D-Glucose, 0.0188 g/250 ml penicillin-G, 0.0125 g/250 ml streptomycin sulfate, 0.0005 g/250 ml phenol red and 0.25 g/250 ml PVA) supplemented with 10 mM Na-lactate, 0.1 mM Na-pyruvate, 2 mM caffeine-sodium benzoate, 3 mM Ca-lactate2pentahydrate and 75 mg of BSA (fraction V). Sperm was prepared by centrifuging the semen twice at 1400 RPM for 5 min before diluting with TALP-fertilization medium and sperm wash (composed of 50 ml M199 supplemented with 5 mg Na-pyruvate, 45 mg Ca-lactate, 3.75 mg penicillin-G, 2.5 mg streptomycin sulfate and 6 ml heat-inactivated FBS) to give a final sperm concentration of $5 \times 10^6$ sperm/ml. 10 µl of the prepared sperm was added to 90 µl droplets of TALP-fertilization medium containing the matured COCs, to give a final sperm concentration of $5 \times 10^5$ sperm/ml.

Following fertilization, the cumulus cells were removed by repetitive pipetting and the zygotes washed twice through modified PZM-5 (mPZM-5; Yoshioka K et al., 2008, Defined system for in vitro production of porcine embryos using a single basic medium, *Journal Reproduction and Development*, 54(3): 208-213) and then cultured in 100 µl mPZM-5 IVC droplets. Modified PZM-5 culture medium was supplemented with 3 mg/ml of BSA instead of PVA (Yoshioka K et al., 2012, Production of piglets from in vitro-produced embryos following non-surgical transfer, *Animal Reproduction Science*, 131 (1-2): 23-29). Embryos were cultured for 6 days at 38.3° C. in 5.5% $CO_2$ and 7% $O_2$ humidified air. Cleavage was determined on Day 3 and blastocyst development rate was determined on Day 5 and Day 6. Blastocyst development rate was scored based upon morphological appearance, including blastocyst diameter and cavity size. Blastocysts were scored as being either; small-medium, expanded or hatched/hatching.

Differential Staining

For both embryo production methods described above, blastocysts scored as medium, expanded, or hatched/hatching, were differentially stained on Day 6 of culture with Hoechst 33358 and Propidium Iodide (Handyside A and Hunter S., 1984, Rapid procedure for visualising the inner cell mass and trophectoderm nuclei of mouse blastocysts in situ using polynucleotide-specific fluorochromes, *J. Exp. Zool.*, 231: 429-434). The zona pellucida of each embryo was removed in a 200 µl drop of pronase solution under mineral oil and the zona free blastocysts were washed twice in protein free M199 Hepes containing 1 mg/ml PVA. The blastocysts were then incubated in the dark in 60 µl of 10 mM trinitrobenzenesulphonic acid (TNBS) with 740 µl M199 Hepes-PVA, at a pH of 8.5 for 20 min. The blastocysts were then washed three times through M199 Hepes-PVA and then incubated in 10 µl of 0.2 mg/ml anti-DNP BSA with 40 µl M199 Hepes-PVA for 20 min at 37° C. The blastocysts were then washed three times through M199 Hepes-PVA before incubation in 5 µl guinea pig complement with 10 µg/ml Hoechst 33342 (1 mg/ml stock), 10 µg/ml Propidium iodide (0.1 mg/ml stock) and 40 µl M199 Hepes-PVA for 20 mins at 37° C. Following a final wash through M199 Hepes-PVA, the blastocysts were fixed in 99% ethanol and then mounted on a glass slide under glycerol and covered with a cover slip. The cover slip was then sealed with nail polish. The stained embryos were viewed using a UV light source microscope. The inner cell mass stained blue and the trophectoderm cells stained pink.

Porcine GM-CSF

Porcine recombinant GM-CSF was purchased from R&D systems (Minneapolis, Minn.). Lyophilized 10 µg of GM-CSF (product 711-PG-010) was reconstituted to 10 µg/ml in sterile D-PBS containing 0.1% BSA. This solution was further diluted 1:10 in sterile D-PBS containing 0.1% BSA to give a 1 µg/ml (1000×) stock solution and stored at −20° C. until use. This stock solution was then diluted either 1:500 or 1:100 to give a working concentration of either 2 ng/ml or 10 ng/ml.

Results

The Addition of GM-CSF to Oocyte Maturation Media Increases Blastocyst Inner Cell Mass Cell Numbers in Pigs In the first oocyte maturation and embryo production method, abattoir-derived porcine oocytes were matured in oocyte maturation medium containing 10% porcine follicular fluid with or without supplemented GM-CSF. The effect of GM-CSF on blastocyst inner cell mass number, trophectoderm cell number, and total cell number is shown in Table 3. Treatment with 2 ng/ml GM-CSF significantly increased blastocyst inner cell mass, trophectoderm and total cell numbers by 60.8%, 8.6%, and 12.7%, respectively, compared to the control group.

TABLE 3

Effect of GM-CSF on blastocyst ICM, trophectoderm and total cell number

| GM-CSF (ng/ml) | n | ICM | Trophectoderm | Total |
| --- | --- | --- | --- | --- |
| 0 | 64 | 3.39 ± 0.62 | 39.91 ± 3.24 | 43.30 ± 3.64 |
| 2 | 70 | 5.45 ± 0.52 | 43.33 ± 2.31 | 48.78 ± 2.65 |
| 10 | 76 | 5.35 ± 0.43 | 43.73 ± 2.54 | 48.76 ± 3.01 |

Values are mean ± standard error (SEM) of 5 replicates.

The Addition of GM-CSF to Oocyte Maturation Media Increases On-Time Blastocyst Development and Blastocyst Rate in Pigs In the second oocyte maturation and embryo production method, abattoir-derived porcine oocytes were matured in oocyte maturation medium with or without supplemented GM-CSF and lacking porcine follicular fluid. The effect of GM-CSF on subsequent embryo development is shown in Table 4. Treatment with 2 ng/ml and 10 ng/ml of GM-CSF significantly increased the number of blastocysts present on day 5 of culture by 41% and 78%, respectively. This is the stage that blastocysts would normally form in vivo demonstrating that the addition of GM-CSF to maturation media can overcome the developmental delay seen when embryos are produced and/or cultured in vitro to increase on-time blastocyst development. The addition of GM-CSF to oocyte maturation media also increased the number of blastocysts present at the end of culture on day 6 by 28% and 22%, respectively.

TABLE 4

Effect of GM-CSF on porcine embryo development

| GM-CSF (ng/ml) | n | Cleaved | Day 5 Blastocyst | Day 6 Blastocyst |
| --- | --- | --- | --- | --- |
| 0 | 289 | 65.0 (3.8) | 13.8 (2.1) | 29.5 (4.3) |
| 2 | 275 | 79.8 (3.9) | 19.4 (4.1) | 38.0 (4.3) |
| 10 | 279 | 73.1 (4.9) | 24.6 (3.6) | 36.1 (4.5) |

Values are percentage of total (n) and are mean ± standard error (SEM) of 6 replicates The blastocysts above were differentially stained to determine inner cell mass, trophectoderm and total cell numbers. The results are shown in Table 5. The addition of 2 ng/ml of GM-CSF to the ooycte maturation media increased blastocyst inner cell mass, trophectoderm and total cell numbers by 25%, 11% and 13%, respectively. The addition of 10 ng/ml of GM-CSF to the oocyte maturation media increased blastocyst inner cell mass, trophectoderm and total cell numbers by 29%, 16% and 19%, respectively compared with the control group.

TABLE 5

Effect of GM-CSF on blastocyst ICM,
trophectoderm and total cell number

| GM-CSF (ng/ml) | n | ICM | Trophectoderm | Total |
|---|---|---|---|---|
| 0 | 81 | 7.38 (0.9) | 38.3 (2.3) | 45.7 (2.5) |
| 2 | 101 | 9.25 (1.0) | 42.5 (3.0) | 51.6 (4.0) |
| 10 | 98 | 9.55 (1.5) | 44.3 (2.9) | 54.5 (4.6) |

Values are mean ± standard error (SEM) of 6 replicates.

Example 2

Effect of GM-CSF on Maturation of Bovine Oocytes In Vitro

The effect of adding granulocyte macrophage-colony stimulating factor (GM-CSF) to oocyte maturation media was examined in cows in dose response experiments using recombinant GM-CSF. Embryos were produced using in vitro embryo production systems.

Experiments examined the number of embryos that cleaved and developed to the blastocyst stage as well as blastocyst inner cell mass, trophectoderm and total cell numbers as measures of oocyte developmental competence. All chemicals were purchased from Sigma-Aldrich unless otherwise stated.

Methods

Bovine GM-CSF

Bovine recombinant GM-CSF was purchased from Kingfisher Biotech, Inc. (St Paul, Minn.). Lyophilized 25 µg of GM-CSF (product RP0871B-025) was reconstituted to 25 µg/ml in sterile D-PBS containing 0.1% BSA. This solution was further diluted 1:10 in sterile D-PBS containing 0.1% BSA to give a 1 µg/ml (1000×) stock solution and stored at −20° C. until use. This stock solution was then diluted either 1:500 or 1:100 to give a working concentration of either 2 ng/ml or 10 ng/ml.

Oocyte Maturation and In Vitro Embryo Production

Oocyte Collection and In Vitro Maturation

Ovaries were collected and transported from a local abattoir in saline at 30-35° C. Follicles between 2 and 8 mm in diameter were aspirated using an 18-gauge needle and 10 ml syringe. COCs with tight cumulus and ungranulated oocytes were then selected in clean follicular fluid, washed twice through wash media (Vitrowash, IVF Vet Solutions)+4.0 mg/ml BSA, and in vitro maturation (IVM) media (Vitromat, IVF Vet Solutions, Robinson Research Institute, University of Adelaide, SA, Australia) supplemented with 4.0 mg/ml BSA and 0.1 IU/ml FSH (Ovagen). The COCs were then transferred into equilibrated IVM medium culture drops (500 µl drops) covered with paraffin oil (Merck). Maturation treatment groups were: (1) control (IVM medium), (2) 2 ng/ml GM-CSF (IVM medium+2 ng/ml GM-CSF), and (3) 10 ng/ml GM-CSF (IVM medium+10 ng/ml GM-CSF). Groups of 50 COCs were cultured in 500 µl media for 23 hrs at 38.5° C. with 6% $CO_2$ in humidified air.

In Vitro Fertilization (IVF) and In Vitro Culture (IVC)

After maturation, the COCs were washed through wash medium (Vitrowash, IVF Vet Solutions)+4.0 mg/ml BSA, and transferred into 500 µl culture drops of IVF medium (Vitrofert, IVF Vet Solutions)+4.0 mg/ml BSA+10 IU Heparin+25 µM penicillamine+12.5 µM hypotaurine+1.25 µM epinephrine covered with paraffin oil. Sperm was supplied by Semex Australia Pty Ltd from a fertility proven bull. Two straws of sperm were thawed at 30-35° C. and prepared using a Bovipure discontinuous gradient (40%:80%) and added at a final concentration of $1\times10^6$ sperm/ml. COCs were incubated with sperm for 23 hrs in 6% $CO_2$ in air before being mechanically denuded by repeat pipetting and washed through wash media (Vitrowash, IVF Vet Solutions)+4.0 mg/ml BSA, and groups of 5 embryos were transferred into 20 µl drops of pre-equilibrated cleavage medium (Vitrocleave, IVF Vet Solutions)+4.0 mg/ml BSA covered with paraffin oil and incubated at 38.5° C. in 7% $O_2$, 6% $Co_2$ and balance of $N_2$ for 5 days. On day 5, embryos were transferred to 20 µl culture drops of pre-equilibrated blastocyst medium (Vitroblast, IVF Vet Solutions)+4.0 mg/ml BSA covered with paraffin oil at 38.5° C. in 7% $O_2$, 6% $Co_2$ and balance of $N_2$ until day 8.

Results

The Addition of GM-CSF to Oocyte Maturation Media Increases Blastocyst Development in Cattle Abattoir-derived bovine oocytes were matured in oocyte maturation media with or without supplemented GM-CSF. The effect of GM-CSF on subsequent embryo development is shown in Table 6. The addition of 2 ng/ml and 10 ng/ml of GM-CSF increased the number of blastocysts present on day 8 of culture by 20% and 44%, respectively, compared with the control group.

TABLE 6

Effect of GM-CSF on bovine embryo development

| GM-CSF (ng/ml) | n | Cleaved | Day 8 Blastocyst |
|---|---|---|---|
| 0 | 179 | 92 (3.5) | 36.9 (5.9) |
| 2 | 173 | 88 (6.1) | 44.1 (5.6) |
| 10 | 160 | 89 (5.7) | 53.2 (5.6) |

Values are percentage of total (n) and are mean ± standard error (SEM) of 4 replicates The Addition of GMCSF to Oocyte Maturation Media Increases the Proportion of Bovine Blastocysts that are Hatched Blastocysts on Day 8 of Embryo Culture As shown in FIG. 1, treatment with 2 ng/ml and 10 ng/ml of GM-CSF significantly increased the proportion of total bovine blastocysts that reached the hatched blastocyst stage on day 8 of embryo culture by 45.4% and 149.0%, respectively. This is the stage that blastocysts would normally form in vivo demonstrating that the addition of GM-CSF to maturation media can overcome the developmental delay seen when bovine embryos are produced and/or cultured in vitro to increase on-time blastocyst development.

Demonstration of an efficacy for the use of GM-CSF in maturing bovine oocytes in vitro is important given that the beef and dairy cattle industries already use IVM routinely for breeding purposes, and cattle embryos are often used as a model for effects on human embryos.

Example 3

Effect of GM-CSF on Maturation of Murine Oocytes In Vitro

The effect of adding granulocyte macrophage-colony stimulating factor (GM-CSF) to oocyte maturation media was examined in mice in dose response experiments using recombinant GM-CSF. Embryos were produced using in vitro embryo production systems. Experiments examined the number of embryos that cleaved and developed to the blastocyst stage as well as blastocyst inner cell mass, trophectoderm and total cell numbers as measures of oocyte developmental competence. All chemicals were purchased from Sigma-Aldrich unless otherwise stated.

Mice

CBAFI males (6-8 weeks) and females (21-23 days) were housed under a 12 h light and 12 h dark cycle with ad libitum access to water and food. All experiments were performed in accordance with Australian Code of Practice for the care and the Use of Animals for Scientific Purpose and the study was approved by the University of Adelaide Animal Ethics Committee (M/2015/072 and M/2017/081).

Murine GM-CSF

Murine recombinant GM-CSF was purchased from R&D systems (Minneapolis, Minn.). Lyophilized 10 µg of GM-CSF (product 415-ML-010) was reconstituted to 10 µg/ml in sterile D-PBS containing 0.1% BSA. This solution was further diluted 1:10 in sterile D-PBS containing 0.1% BSA to give a 1 µg/ml (1000×) stock solution and stored at −20° C. until use. This stock solution was then diluted either 1:500 or 1:100 to give a working concentration of either 2 ng/ml or 10 ng/ml.

Oocyte Maturation and In Vitro Embryo Production

Oocyte Collection and In Vitro Maturation

C57Bl6×CBA F1 female mice were administered with equine chorionic gonadotropin (eCG; Folligon, Intervert, Boxmeer, The Netherlands) via intraperitoneal injection (i.p) to stimulate follicle growth. 46-48 h post-injection, cumulus oocyte complexes (COCs) were aspirated from large antral follicles and collected in HEPES-buffered minimum essential medium ($\alpha$-MEM) handling media supplemented with 4.0 mg/ml bovine serum albumin (BSA) and 1 mg/ml Fetuin (Wong S L et al., 2015, Hyperglycaemia and lipid differentially impair mouse oocyte developmental competence, *Reproduction, Fertility and Development*, 27: 583-592). IVM Media was pre-equilibrated in an incubator (37° C., 6% $O_2$) for 4 h before performing IVM. Ten COCs were cultured per 50 µl drop of IVM media in 20% $O_2$, 6% $CO_2$, and $N_2$ as balance for 16 h. The IVM culture medium was bicarbonate-buffered $\alpha$-MEM containing 3 mg/ml BSA and 1 mg/ml Fetuin and 5 mIU/ml FSH (Puregon-Organon, Oss, The Netherlands; Wong S L et al., 2015, supra) 16 h post-maturation, cumulus expansion was assessed using a scale as described in Vanderhyden B C et al., 1990 (Developmental pattern of the secretion of cumulus expansion-enabling factor by mouse oocytes and the role of oocytes in promoting granulosa cell differentiation, *Developmental Biology*, 140: 307-317). COCs were graded as 0: no expansion, 1+: outer layer of cumulus cells expanded, 2: outer half of cumulus expanded, 3: all layers expanded apart from corona radiatae, and 4+: maximum expansion of all layers of cumulus cells.

In Vitro Fertilization (IVF) and In Vitro Culture (IVC)

C57Bl6×CBA F1 male mice were sacrificed using cervical dislocation and the Vas deferens along with the epididymis dissected out and placed in Wash Media (Cook Medical Pty. Ltd, QLD, Australia) at 37° C., and excess tissue and fat removed under microscope. The vas deferens and epididymis were then transferred into a culture dish containing pre-equilibrated 1000 µl Fert Media (Cook Medical Pty. Ltd, QLD, Australia) and spermatozoa extracted and incubated for 45-60 min at 37° C. in 6% $CO_2$, 5% $O_2$, and 89% $N_2$ to allow the sperm to capacitate (Wong S L et al., 2015, supra) Spermatozoa, were then added to the fertilization drop containing expanded COCs and incubated for 4 h. Following fertilization presumptive zygotes were cultured in Cleave Media (Cook Medical Pty Ltd, QLD, Australia) until day 5. Preimplantation embryo development was determined by examining cleavage rate as a measure of fertilization and blastocyst rates on days 4 and 5.

Differential Staining

ICM and trophectoderm (TE) cell numbers were determined using differential staining as described (Handyside A and Hunter S., 1984 supra). Blastocysts were placed in 20 µl of 0.5% pronase for about 2-3 min until the zona pellucida was dissolved and then placed in protein free 3-(N-morpholino) propanesulfonic acid (MOPS) media. These were then transferred into 10 µl of 2,4,6-trinitrobenzenesulfonic acid and 90 µl of plolyvinylpyrrolidone (PVP) and cultured at 4° C. for 10 min. Blastocysts were then incubated in 20 µl of anti-dinitrophenyl for 10 minutes at 37° C. and then incubated in complement (50 µl propidium iodide (P1) and 50 µl guinea pig serum) at 37° C. for 5 min. Blastocysts were then transferred to 500 µl of bisbenzimide and incubated overnight at 4° C. The following day embryos were placed in 500 µl of 100% ethanol and placed on a siliconised slide in 3 µl of glycerol. A coverslip was gently placed on top of the drop and the number of ICM cells (blue) and TE (pink) counted under UV and red filter. Blastocysts were imaged using Olympus BX 51 (Olympus, Victoria, Australia) fitted with an ultraviolet lamp. Bisbenzimide was excited and emitted at 338 nm and 505 nm to visualise ICM cells and PI at 537 nm and 619 nm to visualise TE cells.

Blastocyst DNA Damage

The histone modification antibody $\gamma$H2AX (Cell Signalling Technology) was used to measure the incidence of DNA double strand breaks as an estimate of blastocyst DNA damage (Sharma A et al., 2012, Histone H2AX phosphorylation: A marker for DNA damage, *Methods in Molecular Biology*, 920: 613-626). Embryos were fixed in 4% paraformaldehyde and then washed for 30 min in phosphate buffered saline (PBS) with 0.3 mg/ml polyvinyl alcohol (PVA) and permeabilised in 0.25% Triton-X (USB Corporation, OH). To prevent non-specific binding, 10% blocking solution of goat serum in PBS-PVA (Jackson ImmunoResearch, PA) was added for 1 h. Blastocysts were then incubated overnight at room temperature (RT) with primary antibody $\gamma$H2AX in 10% goat serum (in PBS-PVA). No primary antibody was used in the negative control. On Day 2, blastocysts in treatments were washed in PBS-PVA solution for 3 times for 2 min each. Blastocysts were then labelled with secondary antibody, Alexa-594 (Life Technologies) at a dilution factor of 1:500 and incubated for 2 h at room temperature. Along with secondary antibody, 4'6 dimidino-2-phenylindole (DAPI) was added as a nuclear stain. Post-incubation embryos were washed three times in PBS and were loaded into a confocal dish for imaging. Fluorescence was detected by a Fluoview FV10i confocal microscope (Olympus, Tokyo, Japan). Instrument settings were kept constant for each replicate. The experiment was replicated five times with at least 10 blastocysts evaluated per treatment.

Vitrification/Warming

Mouse blastocyst were collected on day 5 and vitrified prior to embryo transfer to pseudopregnant recipient mice. Vitrification mediums were made on the day vitrification was performed. For vitrification, the handling media (HM) contained BSA, the equilibrium solution consisted of 8 ml handling media, 1 ml ethylene glycol (EG), 1 ml dimethyl sulphoxide (DMSO), and the vitrification solution consisted of 10.8 ml sucrose media (SM), 1.2 ml handling media, 3 ml DMSO and 3 ml ethylene glycol. 600 µl was taken from each media and placed in a 4-well nunc dish which was equilibrated at 37° C. for 15 min before performing vitrification. 6-7 blastocyst were transferred into each well containing handling media and then immediately placed in another well containing handling media, then into well 3 with equilibrium solution for 3 min at 37° C. and then into vitrification solution for 20-30 sec at 37° C. before placing it onto the hook of the straw which was then inserted into precooled fibre plug and stored in liquid nitrogen. Warming media was made on the morning of embryo transfer and equilibrated at 37° C. for 15 min before use. Warming solution (WS) 1 consisted of 7 ml HM and 3 ml of SM, WS2 consisted of 7.5 ml of HM and 2.5 ml of SM, WS3 had 8.5 ml of HM and 1.5 ml of SM, while WS4 consisted of 10 ml of HM. 500 µl was taken from WS1 and WS2 while 600 µl from WS3 and WS4 and placed in a 4-well nunc dish which was calibrated at 37° C. for 15 min before warming. Blastocysts were warmed by removing the fibre plug and placing the straw containing the blastocyst in a well with WS 1. Blastocysts were then immediately placed in WS 2 for 5 min, then into WS 3 for 5 min and then into WS 4 for 5 min after which they were placed into pre-equilibrated Cleave Media. Prior to transfer, blastocysts were cultured for 3-4 h in Cleave Media (Cook Medical Pty Ltd, QLD, Australia) to allow them to re-expand in order to determine survival rate before being transferred.

Pseudopregnancy and Embryo Transfer

Swiss female mice aged between 8-12 weeks were used as recipient mothers for embryo transfer. These were placed with vasectomised adult C57Bl6×CBA FI males in order to induce pseudopregnancy. On day 2.5 dpc blastocysts from control and 10 ng/ml GM-CSF groups were surgically transferred to contralateral uterine horns (Zander-Fox D L et al., 2015, Reduction of mitochondrial function by FCCP during mouse cleavage stage embryo culture reduces birth weight and impairs the metabolic health of offspring, *Biology of Reproduction*, 92: 124). Six re-expanded blastocysts from each group were transferred to one horn chosen at random. A total of 11 transfers were undertaken for each treatment group. Mice were culled on day 17.5 of pregnancy and the number of implantations and foetuses determined. Fetal weight, crown rump length and diameter and placental weight were also determined.

Results

The Addition of GM-CSF to Defined Oocyte Maturation Media Increases on Time Blastocyst Development and Blastocyst Rate in Mice Mouse oocytes derived from hormonally stimulated prepubertal mice were matured in oocyte maturation media with or without supplemented GM-CSF. The effect of GM-CSF on subsequent embryo development is shown in Table 7.

TABLE 7

Effect of GM-CSF on murine embryo development

| GM-CSF (ng/ml) | n | Cleaved | Day 4 Blastocyst | Day 5 Blastocyst |
|---|---|---|---|---|
| 0 | 223 | 87.3 (13.9) | 13.8 (2.1) | 29.5 (4.3) |
| 2 | 251 | 89.0 (7.4) | 19.4 (4.1) | 38.0 (4.3) |
| 10 | 226 | 88.4 (7.0) | 24.6 (3.6) | 36.1 (4.5) |

Values are percentage of total (n) and are mean ± standard error (SEM) of 6 replicates The addition of 2 ng/ml and 10 ng/ml of GM-CSF significantly increased the number of blastocysts present on day 4 of embryo culture by 41% and 78%, respectively. This is the stage that blastocysts would normally form in vivo demonstrating that the addition of GM-CSF to maturation media can overcome the developmental delay seen when embryos are produced and/or cultured in vitro to increase on-time blastocyst development. The addition of 2 ng/ml and 10 ng/ml GM-CSF to oocyte maturation media also increased the total number of blastocysts present at the end of culture on day 6 by 28% and 22%, respectively.

Figure 2:
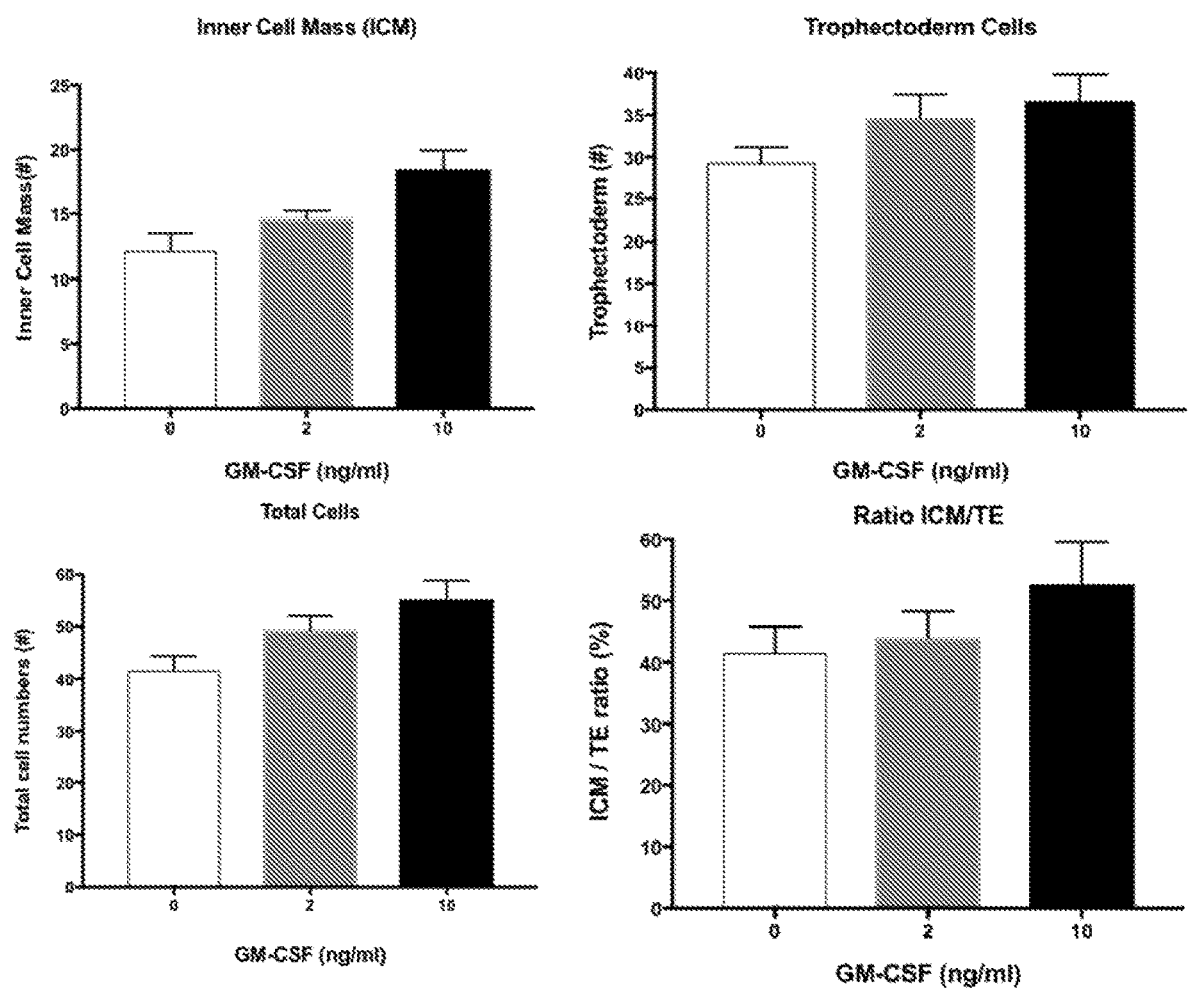
FIG. 2—graphs showing the effect of adding GM-CSF to oocyte maturation media on blastocyst inner cell mass, trophectoderm and total cell numbers. The addition of GM-CSF to oocyte maturation media increased murine blastocyst ICM and total cell numbers by 20.5% and 52.1%, trophectoderm cell numbers by 18.2% and 25.0%, and total cell numbers by 18.8% and 32.9%, respectively. 0 ng (control; white), 2 ng/ml GM-CSF (grey), and 10 ng/ml GM-CSF (black). Values mean±SEM of six replicates.

The Addition of GM-CSF to Maturation Media Increases Blastocyst Cell Numbers in Mice The blastocysts above were differentially stained to determine inner cell mass, trophectoderm and total cell numbers. The results are shown in FIG. 2. The addition of 2 ng/ml and 10 ng/ml of murine GM-CSF to oocyte maturation media increased blastocyst inner cell mass by 20.5% and 52.1%, trophectoderm cell number by 18.2% and 25.0%, and total cell number by 18.8% and 32.9%, respectively.

Figure 3:
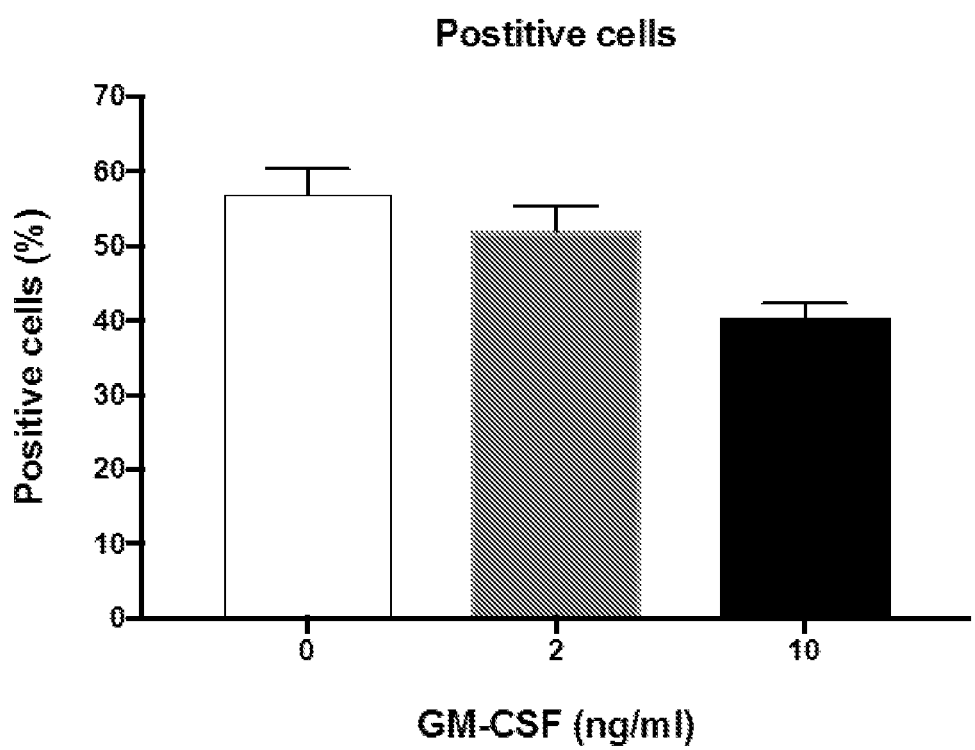
FIG. 3—a graph showing the effect of adding GM-CSF to oocyte maturation media on murine DNA blastocyst damage. The addition of GM-CSF to maturation media reduced the incidence of DNA double strand breaks in the 2 ng/ml GM-CSF and 10 ng/ml GM-CSF groups by 8.4% and 29.1%, respectively, compared with the control. Values are expressed as a percentage and are the mean±SEM of five replicates.

The Addition of GM-CSF to Oocyte Maturation Media Reduces the Incidence of DNA Damage in Murine Blastocysts The incidence of DNA damage was determined in murine in vitro produced blastocysts by examining the incidence of γH2AX staining using immunohistochemistry in control and blastocysts produced using oocytes matured in maturation media containing 2 ng/ml and 10 ng/ml of GM-CSF. The results are shown in FIG. 3. The addition of GM-CSF reduced the proportion of positive cells in the 2 ng/ml and 10 ng/ml groups by 8.4% and 29.1%, respectively compared with the control.

The Addition of GM-CSF to Oocyte Maturation Media Increases Pregnancy and Implantation Rates in Mice Control and blastocysts produced using oocytes matured in maturation media containing 10 ng/ml of GM-CSF were vitrified and warmed. Vitrified blastocysts which expanded following warming were transferred to contralateral (opposite) uterine horns chosen at random of recipient mice. Mice were sacrificed on day 17.5 post coitus and the number of implantations and foetuses determined.

Figure 4:
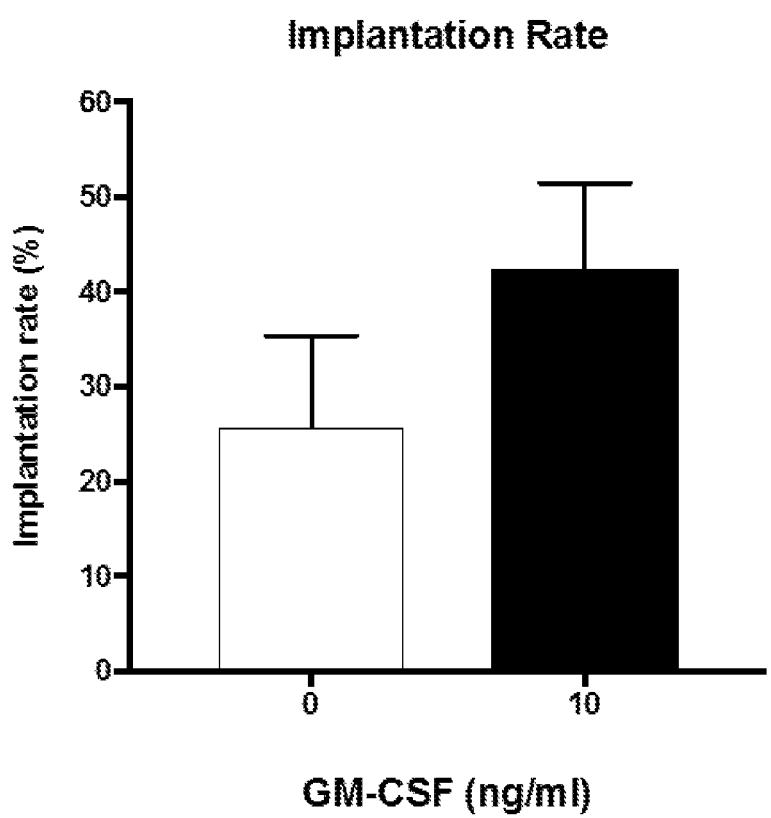
FIG. 4—a graph showing the effect of maturing murine oocytes with GM-CSF on implantation rate. Values are expesed as a percentage of the number of implantation sites/embryos transferred and are the mean±SEM of 11 transfers.

Pregnancy rate as determined by the number of horns which had implantations/foetuses present was increased by 50% in the GM-CSF group. As shown in FIG. 4, implantation rate was increased by 64.7% in the GM-CSF group.

The Addition of GM-CSF to Oocyte Maturation Media Increases Birth Rate in Mice

Figure 5:
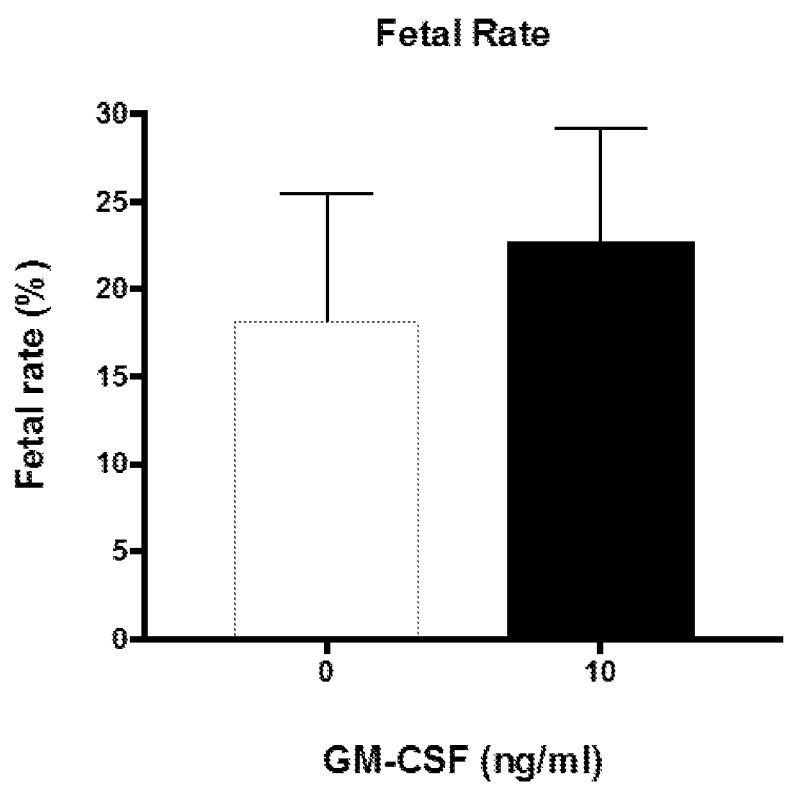
FIG. 5—a graph showing the effect of maturing murine oocytes with GM-CSF on the number of fetuses present at day 17.5 post coitus. Values are expesed as a percentage of fetuses present/embryos transferred and are the mean±SEM of 11 transfers.

Control and blastocysts produced using oocytes matured in media containing 10 ng/ml GM-CSF were vitrified and warmed. Vitrified blastocysts which expanded following warming were transferred to contralateral or opposite horns of recipient mice and the number of fetuses present on day 17.5 were used to measure birth rate. As shown in FIG. 5, birth rate was increased in the GM-CSF group by 25% compared with the control group.

SUMMARY

The results from Examples 1 to 3 show that the addition of GM-CSF to oocyte maturation media can increase oocyte developmental competence. This results in marked improvement in embryo quantity and quality, which in turn increases implantation and birth rates. In particular, the present invention demonstrates the surprising and unexpected findings that the addition GM-CSF to oocyte maturation media:

Increases the number of oocytes that develop to the blastocyst stage following fertilisation;

Increases the number of oocytes that reach the blastocyst stage at the same time as that would occur normally in vivo (on-time blastocyst rate) following fertilisation. Embryos produced and/or cultured are delayed in their development compared with their in vivo counterparts highlighting deficiencies of current in vitro maturation fertilisation and culture systems;

Increases the number of blastocysts that hatch. As well as a measure of on-time embryo development, the ability of a blastocyst to hatch from the zona pellucida is used as a measure of embryo viability;

Increases the number of blastocyst inner cell mass cells. The inner cell mass comprises the cells which give rise to the fetus and has been shown previously to correlate with implantation rate.

Increases the number of trophectoderm cells blastocysts contain. These are the cells which contribute to the placenta and as such effects placental growth and development which in turn influences fetal growth and development;

Increases the total number of cells blastocysts contain;

Reduces the incidence of DNA damage in blastocysts demonstrating that the addition of GM-CSF to maturation media reduces the environmental stress associated with in vitro culture;

Increases the number of recipients or surrogates which become pregnant/pregnancy rate following embryo transfer;

Increases the number of cryopreserved blastocysts which implant; and

Increases the number of cryopreserved blastocysts which develop to term.

Example 4

Effect of GM-CSF on Maturation of Oocytes and Embryos In Vitro

The effect that the presence of GM-CSF in a culture medium has on blastocyst development when an oocyte and an embryo derived from the oocyte are cultured in the medium is examined. In effect, it can be determined whether GM-CSF has an additive or even synergistic effect when used in maturation culture media from the oocyte through to the embryo stage.

Oocytes are matured in vitro in media containing GM-CSF according to the methods set out above in Examples 1 to 3. The matured oocytes are then fertilised according to the methods described in Examples 1 to 3 and cultured in culture media with or without GM-CSF present in the culture media.

Fertilisation rate and the number of blastocyst stage embryos present, together with ICM, trophectoderm and total cell numbers are examined as per Examples 1 to 3 to determine whether the addition of GM-CSF to maturation and culture media has an additive or even synergistic effect on blastocyst development. Experiments are replicated a number of times to confirm the added benefit of using GM-CSF media in both the oocyte maturation, fertilisation, and embryo stage culturing of the IVF process.

With respect to pigs, as shown in Table 8, the inventor has demonstrated that the addition of 2 ng/ml and 10 ng/ml of GMCS-F to oocyte maturation media alone increased cleavage rate by 15.7% and 14.4%, respectively. However, the addition of 10 ng/ml of GMCSF to maturation, fertilisation and culture media increased cleavage rate by 25.2% demonstrating an additive effect when GM-CSF is added throughout culture (i.e. from the oocyte through to the embryo stage).

TABLE 8

Effect of GM-CSF on porcine embryo development

| GM-CSF (ng/ml) | n | Cleaved | Day 5 Blastocyst | Day 6 Blastocyst |
| --- | --- | --- | --- | --- |
| 0 | 96 | 66.8 (1.4) | 18.4 (4.8) | 40.7 (0.2) |
| 2 | 96 | 77.3 (9.9) | 18.7 (3.7) | 43.8 (0.9) |
| 10 | 89 | 76.4 (0.8) | 34.8 (0.7) | 48.9 (7.3) |
| 10 + 10 + 10 | 92 | 83.7 (0.4) | 27.9 (7.5) | 52.3 (2.2) |

Values are percentage of total (n) and are mean ± standard error (SEM) of 2 replicates Furthermore, as shown in Table 8, the addition of 2 ng/ml and 10 ng/ml of GM-CSF to maturation media alone increased day 6 blastocyst rate by 7.6% and 20.1%, respectively. However, the addition of 10 ng/ml of GM-CSF to maturation, fertilisation and culture media increased day 6 blastocyst rate by 28.5% demonstrating an additive effect when GM-CSF is added throughout culture.

The invention claimed is:

1. A method of increasing maturation or increasing developmental competence of a mammalian oocyte in vitro, the method comprising culturing the oocyte in vitro in a mammalian oocyte maturation medium comprising species-specific granulocyte macrophage-colony stimulating factor (GM-CSF), wherein the level of maturation or developmental competence is greater than that of a mammalian oocyte of the same species when cultured in a medium which does not comprise GM-CSF, and wherein an embryo derived from the oocyte cultured in the oocyte maturation medium has improved development when compared to an embryo derived from an oocyte of the same species when cultured in a medium which does not comprise GM-CSF.

2. The method of claim 1, wherein the improved development of the embryo is one or more of an increased on time blastocyst development, an increased blastocyst inner cell mass number, increased blastocyst rate, increased trophectoderm cell number, increased blastocyst total cell number, and increased viability.

3. The method of claim 1, wherein the improved development of the embryo is due to decreased DNA damage in a blastocyst derived from the oocyte cultured in the medium.

4. The method of claim 1, wherein the improved development of the embryo is one or more of increased implantation, pregnancy rate, and development to term, in a recipient following transfer of an embryo derived from the oocyte cultured in the medium to the recipient.

5. The method of claim 1, wherein the mammalian oocyte is selected from the group consisting of a human oocyte, a bovine oocyte, a porcine oocyte, an equine oocyte, a canine oocyte, a feline oocyte, a murine oocyte, an ovine oocyte, and a non-human primate oocyte.

6. The method of claim 1, wherein the amount of GM-CSF present in the medium is about 0.1 ng/ml to about 100 ng/ml.

* * * * *

SEQUENCE LISTING

```
<160> NUMBER OF SEQ ID NOS: 16

<210> SEQ ID NO 1
<211> LENGTH: 800
<212> TYPE: DNA
<213> ORGANISM: Homo sapiens

<400> SEQUENCE: 1
acacagagag aaaggctaaa gttctctgga ggatgtggct gcagagcctg ctgctcttgg      60
gcactgtggc ctgcagcatc tctgcacccg cccgctcgcc cagcccagc acgcagccct     120 gggagcatgt gaatgccatc caggaggccc ggcgtctcct gaacctgagt agagacactg     180
ctgctgagat gaatgaaaca gtagaagtca tctcagaaat gtttgacctc caggagccga     240
cctgcctaca gacccgcctg gagctgtaca agcagggcct gcgggggcagc ctcaccaagc     300 tcaagggccc cttgaccatg atggccagcc actacaagca gcactgccct ccaaccccgg     360
aaacttcctg tgcaacccag attatcacct ttgaaagttt caaagagaac ctgaaggact     420
ttctgcttgt catcccctt gactgctggg agccagtcca ggagtgagac cggccagatg     480
```

| | | |
|---|---|---|
| aggctggcca agccggggag ctgctctctc atgaaacaag agctagaaac tcaggatggt | 540 |
| catcttggag ggaccaaggg gtgggccaca gccatggtgg gagtggcctg gacctgccct | 600 |
| gggccacact gaccctgata caggcatggc agaagaatgg gaatatttta tactgacaga | 660 |
| aatcagtaat attttatatat ttatattttt aaaatattta tttatttatt tatttaagtt | 720 |
| catattccat atttattcaa gatgttttac cgtaataatt attattaaaa atatgcttct | 780 |
| acttgaaaaa aaaaaaaaaa | 800 |

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 3
<211> LENGTH: 768
<212> TYPE: DNA
<213> ORGANISM: Bos taurus

<400> SEQUENCE: 3

| | | |
|---|---|---|
| agtcctcaag aggatgtggc tgcagaacct gcttctcctg ggcactgtgg tctgcagctt | 60 |
| ctccgcacct actcgcccac ccaacactgc caccccggccc tggcagcatg tggatgccat | 120 |
| caaggaggcc ctgagccttc tgaaccacag cagtgacact gatgctgtga tgaatgacac | 180 |
| agaagtcgtc tctgaaaagt ttgactccca ggaaccaacg tgcctgcaga ctcgcctgaa | 240 |
| gctgtacaag aacggcctgc agggcagcct cactagtctc atgggctcct tgaccatgat | 300 |
| ggccacccac tacgagaaac actgccacc caccccggaa acttcctgtg aacccagtt | 360 |
| tatcagcttc aaaaatttca agaggaccct gaaggagttc ctttttatca ttccctttga | 420 |
| ctgctgggaa ccagcccaga gtgaagcag gccaaaccag ccagaagtgg aagcttacct | 480 |
| cacagatcgc tgccctccta cccacaaaga gccaaacaaa actcaggatc ttcacactgg | 540 |
| agggaccaca gggagggcca gagctgtagg gggccgctgg cttgttcagg gccatgttga | 600 |
| ccctgataca ggtgtggcag gggaaacggg aaatgtttta cactggcagg atcagcaat | 660 |
| atttatttat atatttatgt atttaatat ttatttattt atttatttaa actcataccc | 720 |

```
catatttatt caagatgttt ttctataata ataaattatt caaagtca            768
```

<210> SEQ ID NO 4
<211> LENGTH: 143
<212> TYPE: PRT
<213> ORGANISM: Bos taurus

<400> SEQUENCE: 4

```
Met Trp Leu Gln Asn Leu Leu Leu Gly Thr Val Val Cys Ser Phe
1               5                   10                  15

Ser Ala Pro Thr Arg Pro Pro Asn Thr Ala Thr Arg Pro Trp Gln His
                20                  25                  30

Val Asp Ala Ile Lys Glu Ala Leu Ser Leu Leu Asn His Ser Ser Asp
            35                  40                  45

Thr Asp Ala Val Met Asn Asp Thr Glu Val Val Ser Glu Lys Phe Asp
        50                  55                  60

Ser Gln Glu Pro Thr Cys Leu Gln Thr Arg Leu Lys Leu Tyr Lys Asn
65                  70                  75                  80

Gly Leu Gln Gly Ser Leu Thr Ser Leu Met Gly Ser Leu Thr Met Met
                85                  90                  95

Ala Thr His Tyr Glu Lys His Cys Pro Pro Thr Pro Glu Thr Ser Cys
                100                 105                 110

Gly Thr Gln Phe Ile Ser Phe Lys Asn Phe Lys Glu Asp Leu Lys Glu
            115                 120                 125

Phe Leu Phe Ile Ile Pro Phe Asp Cys Trp Glu Pro Ala Gln Lys
        130                 135                 140
```

<210> SEQ ID NO 5
<211> LENGTH: 829
<212> TYPE: DNA
<213> ORGANISM: Sus scrofa

<400> SEQUENCE: 5

```
agtgctcaga gagaaaggct aaagtcctca gaaggatgtg gctgcagaac ctgcttctcc    60
tgggcactgt ggtctgcagc atctccgctc ccacccgccc acccagccct gtcaccggc    120
cctggcagca tgtggatgcc atcaaagaag ccctgagcct tctaaacaac agtaatgaca   180
cagcggctgt gatgaatgaa accgtagacg tcgtctgtga atgtttgac ccccaggagc    240
cgacatgcgt gcagactcgc ctgaacctgt acaagcaggg cctgcggggc agcctcacta   300
ggctcaagag ccccttgact ctgttggcca agcactatga gcagcactgc cccctcaccg   360
aggaaacttc ctgtgaaacc cagtctatca ccttcaaaag tttcaaagac agtctgaaca   420
aatttctttt taccatcccc tttgactgct gggggccagt caaaaagtaa agcagcctgc    480
agcagccaga agccagcctt gccgcacgga ttgctcccac tgacagagcc aaaccaaact   540
caggatcttc accgtggagg gaccactggc tggccaaggc tgtaatgggg cacagacttg   600
ccctgggcca tgttgaccct gatacaggcc tggcagggga atggcagat gtttataccc    660
ggcagggatt agcaatattt attaacctat ttatgtattt taatatttat ttatttattt   720
atctatttat ttatttaagc ttgaacttca tatttattca agatgtttta ccataataat   780
aaattattta aaatctgtaa aaaaaaaaaa aaaaaaaaa aaaaaaaa                829
```

<210> SEQ ID NO 6
<211> LENGTH: 144
<212> TYPE: PRT
<213> ORGANISM: Sus scrofa

<400> SEQUENCE: 6

```
Met Trp Leu Gln Asn Leu Leu Leu Gly Thr Val Val Cys Ser Ile
1               5                   10                  15

Ser Ala Pro Thr Arg Pro Pro Ser Pro Val Thr Arg Pro Trp Gln His
            20                  25                  30

Val Asp Ala Ile Lys Glu Ala Leu Ser Leu Leu Asn Asn Ser Asn Asp
        35                  40                  45

Thr Ala Ala Val Met Asn Glu Thr Val Asp Val Cys Glu Met Phe
    50                  55                  60

Asp Pro Gln Glu Pro Thr Cys Val Gln Thr Arg Leu Asn Leu Tyr Lys
65                  70                  75                  80

Gln Gly Leu Arg Gly Ser Leu Thr Arg Leu Lys Ser Pro Leu Thr Leu
                85                  90                  95

Leu Ala Lys His Tyr Glu Gln His Cys Pro Leu Thr Glu Glu Thr Ser
                100                 105                 110

Cys Glu Thr Gln Ser Ile Thr Phe Lys Ser Phe Lys Asp Ser Leu Asn
            115                 120                 125

Lys Phe Leu Phe Thr Ile Pro Phe Asp Cys Trp Gly Pro Val Lys Lys
        130                 135                 140
```

<210> SEQ ID NO 7
<211> LENGTH: 779
<212> TYPE: DNA
<213> ORGANISM: Equus caballus

<400> SEQUENCE: 7

```
atgtggcttc agaacctgct tcttctgggc actgtggttt acagcatgcc cgcacccacc        60
cgccaaccca gccctgtcac tcggccctgg cagcatgtgg atgccatcaa ggaggccctg       120
agccttctga caacagtag tgacactgct gctatcatga tgaaacagt agaagtcgtc         180
tctgaaacgt ttgacgccga ggagctgaca tgcctgcaga ctcgcctgaa gctgtacaaa       240
cagggcttgc ggggcagcct catcaagctc gaaggcccct taaccatgat ggccagccac       300
tacaagcagc actgccccc caccctggaa acttcctgtg caaccccagat gatcaccttc      360
aaaagtttca aaagaacct gaaggatttt ctgtttgaga tcccgtttga ctgctggaac        420
cagcccagaa gtaaggcagg ccttccagct aggagctagc cctgggagct cacctcacag       480
attgctgctg tcccactcac aaagaaccga aactcaggat cttcagcttg agggaccaa        540
agggtgggcc atggctgttg agaacatgga cttgctctgg gccgtactga ccacgatatg       600
ggtgtggtag gggagtaggg gatatttac actggcgggg atcagtaata tttatttata       660
tatttatgta ttttaatatt tatttattta tttatttaag ctcatactcc atatttattc      720
aagatgtttt accattagaa taaattatta aacccaaaa aaaaaaaa aaaaaaaa            779
```

<210> SEQ ID NO 8
<211> LENGTH: 152
<212> TYPE: PRT
<213> ORGANISM: Equus caballus

<400> SEQUENCE: 8

```
Met Trp Leu Gln Asn Leu Leu Leu Gly Thr Val Val Tyr Ser Met
1               5                   10                  15

Pro Ala Pro Thr Arg Gln Pro Ser Pro Val Thr Arg Pro Trp Gln His
            20                  25                  30

Val Asp Ala Ile Lys Glu Ala Leu Ser Leu Leu Asn Asn Ser Ser Asp
        35                  40                  45
```

```
Thr Ala Ala Ile Met Asn Glu Thr Val Glu Val Ser Glu Thr Phe
    50                  55                  60

Asp Ala Glu Glu Leu Thr Cys Leu Gln Thr Arg Leu Lys Leu Tyr Lys
65                  70                  75                  80

Gln Gly Leu Arg Gly Ser Leu Ile Lys Leu Glu Gly Pro Leu Thr Met
                85                  90                  95

Met Ala Ser His Tyr Lys Gln His Cys Pro Pro Thr Leu Glu Thr Ser
            100                 105                 110

Cys Ala Thr Gln Met Ile Thr Phe Lys Ser Phe Lys Lys Asn Leu Lys
            115                 120                 125

Asp Phe Leu Phe Glu Ile Pro Phe Asp Cys Trp Asn Gln Pro Arg Ser
            130                 135                 140

Lys Ala Gly Leu Pro Ala Arg Ser
145                 150
```

<210> SEQ ID NO 9
<211> LENGTH: 809
<212> TYPE: DNA
<213> ORGANISM: Canis lupus

<400> SEQUENCE: 9

```
aggaggatgt ggctgcagaa cctgcttttc ttgggcactg tggtctgcag catctctgca      60
cccacccgct cacccaccct tgtcactcgg ccctctcagc acgtggatgc catccaggaa     120
gccctgagcc ttttgaacaa cagtaatgac gtgactgctg tgatgaataa agcagtaaaa     180
gtggtctctg aagtgtttga ccctgagggg ccaacatgcc tggagacccg cctacagctg     240
tacaaggagg gcctgcaggg cagcctcacc agcctcaaga tcccttaac catgatggcc      300
aatcactata agcagcactg tccccctacc ccggaatctc cctgtgcaac ccagaatatt     360
aacttcaaaa gtttcaaaga gaacctgaag gattttctgt ttaacatccc ctttgactgc     420
tggaaaccag tcaagaagtg aggcagacca gtccagccag gagccagccc agtccagcca     480
gaagccagcc ctgagagcat acctcatacc tcacaagtca ctgcctttct acccatggat     540
tgctgaaact caggatcttc acctttgagg gacaccgggt ggaccaggc agtagaggggg     600
gcatggactt gctctggcca tgctgcccgg ataccagctt ggtatgggga gcggggaatg     660
ttttatactg gcagggatca gtaatattta tttatatatt tatgtatttt aatatttatt     720
tatttattta tttaagatca tactctgtat ttattcaaga cattttacta ttataataaa     780
ttattaaaag cctgttaaaa aaaaaaaa                                        809
```

<210> SEQ ID NO 10
<211> LENGTH: 144
<212> TYPE: PRT
<213> ORGANISM: Canis lupus

<400> SEQUENCE: 10

```
Met Trp Leu Gln Asn Leu Leu Phe Leu Gly Thr Val Val Cys Ser Ile
1               5                   10                  15

Ser Ala Pro Thr Arg Ser Pro Thr Leu Val Thr Arg Pro Ser Gln His
            20                  25                  30

Val Asp Ala Ile Gln Glu Ala Leu Ser Leu Leu Asn Ser Asn Asp
        35                  40                  45

Val Thr Ala Val Met Asn Lys Ala Val Lys Val Ser Glu Val Phe
    50                  55                  60

Asp Pro Glu Gly Pro Thr Cys Leu Glu Thr Arg Leu Gln Leu Tyr Lys
```

```
        65                  70                  75                  80
Glu Gly Leu Gln Gly Ser Leu Thr Ser Leu Lys Asn Pro Leu Thr Met
                85                  90                  95

Met Ala Asn His Tyr Lys Gln His Cys Pro Thr Pro Glu Ser Pro
            100                 105                 110

Cys Ala Thr Gln Asn Ile Asn Phe Lys Ser Phe Lys Glu Asn Leu Lys
        115                 120                 125

Asp Phe Leu Phe Asn Ile Pro Phe Asp Cys Trp Lys Pro Val Lys Lys
    130                 135                 140
```

<210> SEQ ID NO 11
<211> LENGTH: 435
<212> TYPE: DNA
<213> ORGANISM: Felis catus

<400> SEQUENCE: 11

```
atgtggctgc agaacctgct tttcctgggc actgtggtct gcagcatctc tgcacccacc    60
agttcaccca gctctgtcac tcggccctgg caacacgtgg atgccatcaa ggaggctctg   120
agccttctga caacagtagt gaaataact gctgtgatga atgaagcagt agaagtcgtc   180
tctgaaatgt ttgaccctga ggagccgaaa tgcatgcaga ctcacctaaa gctgtacgag   240
cagggcctac ggggcagcct catcagcctc aaggagcctc tgagaatgat ggccaaccat   300
tacaagcagc actgccccct tactccggaa acgccctgtg aaaccagac tatcaccttc   360
aaaaatttca agagaatct gaaggatttt ctgtttaaca tccccttga ctgctgggag   420
ccagaccaga agtaa                                                     435
```

<210> SEQ ID NO 12
<211> LENGTH: 144
<212> TYPE: PRT
<213> ORGANISM: Felis catus

<400> SEQUENCE: 12

```
Met Trp Leu Gln Asn Leu Leu Phe Leu Gly Thr Val Val Cys Ser Ile
1               5                   10                  15

Ser Ala Pro Thr Ser Ser Pro Ser Ser Val Thr Arg Pro Trp Gln His
            20                  25                  30

Val Asp Ala Ile Lys Glu Ala Leu Ser Leu Leu Asn Asn Ser Ser Glu
        35                  40                  45

Ile Thr Ala Val Met Asn Glu Ala Val Glu Val Val Ser Glu Met Phe
    50                  55                  60

Asp Pro Glu Glu Pro Lys Cys Met Gln Thr His Leu Lys Leu Tyr Glu
65                  70                  75                  80

Gln Gly Leu Arg Gly Ser Leu Ile Ser Leu Lys Glu Pro Leu Arg Met
                85                  90                  95

Met Ala Asn His Tyr Lys Gln His Cys Pro Leu Thr Pro Glu Thr Pro
            100                 105                 110

Cys Glu Thr Gln Thr Ile Thr Phe Lys Asn Phe Lys Glu Asn Leu Lys
        115                 120                 125

Asp Phe Leu Phe Asn Ile Pro Phe Asp Cys Trp Glu Pro Asp Gln Lys
    130                 135                 140
```

<210> SEQ ID NO 13
<211> LENGTH: 1033
<212> TYPE: DNA
<213> ORGANISM: Mus musculus

<400> SEQUENCE: 13

```
ggtcagactg cccaggcagg gtgggaaagg cctttaaagc agcccgcagg tgggctgcca      60
gttcttggaa gggcttatta atgaaaaccc cccaagcctg acaacctggg ggaaggctca     120
ctggccccat gtatagctga taagggccag gagattccac aactcaggta gttccccgc      180
cccctggag ttctgtggtc accattaatc atttcctcta actgtgtata aagagctct       240
tttgcagtga gcccagtact cagagagaaa ggctaaggtc ctgaggagga tgtggctgca     300
gaatttactt ttcctgggca ttgtggtcta cagcctctca gcacccaccc gctcacccat     360
cactgtcacc cggccttgga agcatgtaga ggccatcaaa gaagccctga acctcctgga     420
tgacatgcct gtcacgttga atgaagaggt agaagtcgtc tctaacgagt tctccttcaa     480
gaagctaaca tgtgtgcaga cccgcctgaa gatattcgag cagggtctac ggggcaattt     540
caccaaactc aagggcgcct tgaacatgac agccagctac taccagacat actgcccccc     600
aactccggaa acggactgtg aaacacaagt taccacctat gcggatttca tagacagcct     660
taaaaccttt ctgactgata tcccctttga atgcaaaaaa ccaggccaaa aatgaggaag     720
cccaggccag ctctgaatcc agcttctcag actgctgctt tgtgcctgc gtaatgagcc      780
aggaacttgg aatttctgcc ttaaagggac caagagatgt ggcacagcca cagttggaag     840
gcagtatagc cctctgaaaa cgctgactca gcttggacag cggaagacaa acgagagata     900
ttttctactg atagggacca ttatatttat ttatatattt atattttta aatatttatt      960
tatttattta tttattttg caactctatt tattgagaat gtcttaccag aataataaat     1020
tattaaaact ttt                                                       1033
```

<210> SEQ ID NO 14
<211> LENGTH: 141
<212> TYPE: PRT
<213> ORGANISM: Mus musculus

<400> SEQUENCE: 14

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```

<210> SEQ ID NO 15
<211> LENGTH: 495
<212> TYPE: DNA
<213> ORGANISM: Ovis aries

```
<400> SEQUENCE: 15
agtcctcaag aggatgtggc tgcagaacct gcttctcctg ggcactgtgg tctgcagctt      60
ctccgcaccc actcgccaac ccagccctgt cacccggccc tggcagcatg tggatgccat     120
caaggaggcc ctgagccttc tgaacgacag cactgacact gctgctgtga tggatgaaac     180
agtagaagtc gtctctgaaa tgtttgactc ccaggagccg acatgcctgc agactcgcct     240
ggagctgtac aagcagggcc tgcggggcag cctcaccagt ctcacgggct ccttgaccat     300
gatggccagc cactacaaga aacactgccc cccacccag gaaacttcct gtgaaaccca      360
gattatcacc ttcaaaagtt tcaaagagaa cctgaaggat ttccttttta tcattccctt     420
tgactgctgg gaaccagtcc agaagtgaag caggccagac cagccagaag ccagcccaga     480
agcttacctc acaga                                                     495

<210> SEQ ID NO 16
<211> LENGTH: 144
<212> TYPE: PRT
<213> ORGANISM: Ovis aries

<400> SEQUENCE: 16

Met Trp Leu Gln Asn Leu Leu Leu Gly Thr Val Val Cys Ser Phe
1               5                   10                  15

Ser Ala Pro Thr Arg Gln Pro Ser Pro Val Thr Arg Pro Trp Gln His
            20                  25                  30

Val Asp Ala Ile Lys Glu Ala Leu Ser Leu Leu Asn Asp Ser Thr Asp
        35                  40                  45

Thr Ala Ala Val Met Asp Glu Thr Val Glu Val Val Ser Glu Met Phe
    50                  55                  60

Asp Ser Gln Glu Pro Thr Cys Leu Gln Thr Arg Leu Glu Leu Tyr Lys
65                  70                  75                  80

Gln Gly Leu Arg Gly Ser Leu Thr Ser Leu Thr Gly Ser Leu Thr Met
                85                  90                  95

Met Ala Ser His Tyr Lys Lys His Cys Pro Pro Thr Gln Glu Thr Ser
            100                 105                 110

Cys Glu Thr Gln Ile Ile Thr Phe Lys Ser Phe Lys Glu Asn Leu Lys
        115                 120                 125

Asp Phe Leu Phe Ile Ile Pro Phe Asp Cys Trp Glu Pro Val Gln Lys
    130                 135                 140
```